United States Patent [19]

Kumagai et al.

[11] Patent Number: 5,641,661
[45] Date of Patent: Jun. 24, 1997

[54] *PICHIA PASTORIS* ALCOHOL OXIDASE ZZA1 AND ZZA2 REGULATORY REGIONS FOR HETEROLOGOUS GENE EXPRESSION

[75] Inventors: Monto H. Kumagai, Davis; Genadie G. Sverlow, Vacaville, both of Calif.

[73] Assignee: Biosource Technologies, Inc., Vacaville, Calif.

[21] Appl. No.: 220,606

[22] Filed: Mar. 25, 1994

Related U.S. Application Data

[63] Continuation-in-part of Ser. No. 37,618, Mar. 25, 1993, abandoned, and a continuation-in-part of Ser. No. 37,617, Mar. 25, 1993, abandoned.

[51] Int. Cl.$^6$ ............................ C12P 7/06; C12N 15/00; C12N 1/19; C12N 1/16
[52] U.S. Cl. .................. 435/161; 435/172.3; 435/254.2; 435/254.21; 435/254.23; 536/24.1
[58] Field of Search ............................ 435/161, 172.3, 435/203, 254.21, 254.23, 254.2; 536/23.2, 24.1

[56] References Cited

PUBLICATIONS

Kumagai, Gene, 94:209–216 (1990).
Cregg et al., Bio/Technology 5:1305–1308 (1987).
Cregg et al., Mol. Cell. Biol., 9:1316–1323 (1989).
Koutz et al., Yeast 5:167–177 (1989).
Filho et al. Bio/Technology, 4:311–315 (1986).
Inlow et al. Biotech. & Bioengin., 32:227–234 (1988).
Cohen et al., Mol. Cell. Biol., 7:2753–2761 (1987).

*Primary Examiner*—Nancy T. Vogel
*Attorney, Agent, or Firm*—Albert P. Halluin; Pennie & Edmunds

[57] ABSTRACT

Two novel genomic clones, ZZA1 and ZZA2, were isolated which encode for *Pichia pastoris* alcohol oxidase isozymes. The 5' non-coding region of ZZA1 contains common structural features involved in the transcription and translation of eukaryotic genes. Comparison of the nucleotide sequences of the ZZA1 and AOX1 51 noncoding regions showed that they are 66% similar to each other.

The rice α-amylase gene OS103 was placed under the transcriptional control of the ZZA1 promoter. The nucleotide sequences of ZZA1 and other methanol-regulated promoters were analyzed. A highly conserved sequence (TTGNNNGCTTCCAANNNNNTGGT) (SEQ ID NO:2) was found in the 51 flanking region. A yeast strain containing the ZZA1-OS103 fusion and secreting biologically active a-amylase into the culture media while converting starch to ethanol was produced. The ZZA1 and ZZA2 regulatory sequences may be used to contol the expression of other heterologous proteins in multiple yeast species.

Methods of purifying proteins that are regulators of alcohol oxidase expression (referred to as AOER proteins) and methods of isolating these proteins are also provided.

The invention also provides for the efficient conversion of starch into ethanol.

5 Claims, 18 Drawing Sheets

```
TTCTCCTGGCACTATTTTGCTTCTTATCAGTCTATCTTTGAGTTGGTGAATATCTTGAGA    ZZA1
 ||          |       ||  ||||| ||||||   ||  || ||||||||||| |
TTTCTTCTCGTACGAGCTTGCCCTGATCAGCCTATCTCGCAGCTGATGAATATCTTGTGG    AOX1

CATGGGCTTGGGGAAATCATTTGATTTCGAAGTTTTGCTTGGTAGTTGACATTCTTCTTC    ZZA1
|  |||  |||||  |||||||  ||  ||  ||  |||||  ||||||  ||    |||||
TAGGGGTTTGGGAAAATCATTCGAGTTTGATGTTTTCTTGGTATTTCCCACTCCTCTTC    AOX1

GGAGTATAAAAGATTTAGTGAGACGTTCGTTTGTGCAAGCTT    ZZA1
|||||  |  ||||||   ||||||||||||||||||||||||
AGAGTACAGAAGATTAAGTGAGACGTTCGTTTGTGCAAGCTT    AOX1
```

FIG.5A

```
TTCTCCTGGCACTATTTTGCTTCTTATCAGTCTATCTTTGAGTTGGTGAATATCTTGAGA    ZZA1
||      |   |    |          |||  |     ||   |            |
TTTCATTTCTTTTTATACGTACGTATATGTACTAGATGAAGAATGCGACAAGGCCGACCA    AOX2

CATGGGCTTGGGGAAATCATTTGATTTCGAAGTTTTGCTTGGTAGTTGACATTCTTCTTC    ZZA1
   | | |                ||||  |         ||    || |  | |||
ACAGCAATGGTGCTTGGTACCAAAGTTTGGAAGGTGCTACCGAATTGGCCGATGATATTG    AOX2

GGAGTATAAAAGATTTAGTGAGACGTTCGTTTGTGCAAGCTT    ZZA1
         ||
AGTGGAGTTGTCATTCT                              AOX2
```

FIG.5B

PstI
CTGCAGCTTTGATACCTGAAATTCCTGAGCCTATAATAATGACTTTTGCACTCTGTTGGCTCATGACGAT     -867

SacI
TTTGTTGAAATGAATCTTCACAAGAAGAGCTCAATTGAGTAGAGATAATTAGTAAGTGAGATCCAACACC     -797

CAGGAACGAGATGGATTCAGGAGAAATTGTTCTGCCATCCGACATCGACAAGTTAGACACAATAGTGCCA     -727

AATGCAGAGGGGACGTTTCCTCAAGGCAAGAACTCCACTTTATTCCTCCTCAAACACCCGCCTTCGCCGT     -657

SpeI
TAAAAACCAGCCCAGTTACTAAACATGGTTTGGACTCTCTCTAATCCACTTTGTTAGGCTACTAGTAGCA     -587

TTATTTTCTTAGCCTGTCTATATGGTTCCTTGCGAGTTTTTAATTTTATTTCTATTTCCGAATGTAACTT     -517

ACTCCGCATTCCATCCCAACACCAGAAAGTTGAGGGTTTTTGTGAGTGTGGGGTCGGTAACAGTTTCATG     -447

TTCCCCCAATGGCCTAAAATTGACACTTTAGACGCCCTGTTCAAACTCAAATTGACAAAAGCGTGATCTC     -377

ATCAGAGATGAACTAGGTTTGGTTCGATCAAAAGCTAACGGCCAGTTGGTCAAAAAGAAACTTCCAATGT     -307

EcoRI
CGGCATACCGTTTGTTTCGTTTGACCCGACAATTGATGTTGAAGAATTCCCTCTTACACTTAGCGCAGCC     -237

TTTATTTTGCTTGGGGTCTCGCTGCGCTTGGGTCTCGGTGTGCTTGTGACCGGAAACGCAAATGGGGAAA     -167

NsiI          BstXI
CACCCGCTTTTTGGATGATTATGCATTGTTCTCCACATTGTATGCTTCCAAGTTTCTGGTGGGAATACTG     -97

ATAGCCTAACGTTCATGATCAAAACTAATGTCTTCCCTACTTGAACAGCAATATATAAACAGAAGAAGAT     -27

TTCCTTTCTAAGGTCTTTTTTTTTATCATCATTATCAGCTTACTTTCATAATTGTGACTGGTTCCAATTG     +44

HindIII                           BstBI
ACAAGCTTTTGATTCTAACGACTTTAACGACAACCTAAAGAACAAAAACAACTAATTATTCGAAACAATG     +114
                                                          Met
                                 BamHI
GCT ATT CCC GAA GAA TTT GAT ATT ATC GTC TGT GGT GGT GGA TCC    +159
Ala Ile Pro Glu Glu Phe Asp Ile Ile Val Cys Gly Gly Gly Ser

FIG.9

```
ZZA1  GTAAGTGACATCCAACACCCACGAACGAGATCCATTCAGGAGAAATTGTTCTGCCATCCGACATCGACAAGTTACACACAATAGTGCCAAATGCAGAGCGGACGTTTCCT  -706
         |   |||||| ||  |  |     |   |  ||| ||    |  ||     |   |||  ||| ||| ||  | |
AOX1  TCTAACAT..CCAAAGACGAAACGTTGAATGAAACCTTTTTGCCATCCGACATCCACAGGTCCATTCTCACACATAAGTGCCAAACGCAACAGGACGGGATACACTACCA  -702

ZZA1  CAAGGCAAGAACTCCACTTTATTCCTCCTCAAA.CACCCGGCTTCGCCGTTAAAAACCAGCCCAGTTACTAAACATGGTTTGGACTCTCTCTAATCCACTTTGTTAGGCT  -597
          |     |   || ||||||  | |||      ||||| |    |||| ||| || ||| | |  | |||||||
AOX1  GCAGACGTTGCAAACGCAGGACTCATCCTCTTCTCTAACACCATTTTGCATGAAAACAGCCAGTTATGGGCTTGATGGAGCTCCCTCATTCCAATTCCTTCTATTAGGCT  -592

ZZA1  ACTAGTACCATTATTTTCTTAGCCTGTCTATATGGTTCCTTGCCAGTTTTTAATTTTATTTCTATTTCCGAATGTAACTTACTCCGCATTCCATCCCAACACCAGAAAGT  -487
      ||||  |||| |||  |||||||||||||||||||  | ||  | || || | ||||||||||| |||  ||||||||| || |||| ||
AOX1  ACTAACACCATGACTTTATTAGCCTGTCTATCCTGGCCCCCCCTGGCGACGTCATGTT.TGTTTATTTCCGAATGCAACAAGCTCCGCATTACACCCGAACATCACTCCAG  -483

ZZA1  TGACGGTTTTTGTGAGTGTCGGCTCGGTAACAGTTTCATGTTCCCCCAATGCCCTAAAATTGACACTTTACACGCCCTGTTCAAACTCAAATTGACAAAAGCCTGATCTC  -377
       || |||  ||||||||||||||  || ||||||||| ||||||  |||||| |||||| ||||||| ||| |||| ||| ||| || || || |||||||||||||||||
AOX1  ATGACGGCTTTCTGAGTGTGGGGTC...AAATAGTTTCATGTTCCCA.AATGCCCAAAACTGACAGTTTAAACCCTGTCTTGCAACCTAATATGACAAAACCGTGATCTC  -376

ZZA1  ATCAGACATGAACTAGGTTTGGTTCCATCAAAAGCCTAACCGCCAGTTGGTCAAAAGAAACTTCCAAT.GTCGGCATACCGTTTGTTTCGTTTGACCCGACAATTGATGT  -268
      ||| |||||||||||| |||||||||| ||||||||| ||||||||||||| ||||||||||||||    || ||||||| ||||| || ||||
AOX1  ATCCAAGATGAACTAAGTTTGGTTCCTTGAAATCCTAACCGCCAGTTGGTCAAAAGAAACTTCCAAAGTCGCCATACCGTTTGTCTTGTTTGG.........TAT  -278

ZZA1  TGAAGAATTCCCTCTTACACTTAGCCCAGCCTTTATTTTGCTTGGCGTCTCGCTGCGCTTGGGTCTCGGTGTGCTTGTGACCCCAAACGCAAATGCGGAAACACCCGCTT  -158
      ||| |   || ||    ||||  |  |  ||||  | ||  | |  |  ||||   ||| ||  |  ||||  ||||||
AOX1  TGATTCACCAATGCTCAAAAATAATCTCATTAATGCTTAGCGCAGTCTCTCTATCGCTTCTGAACCCGGTGGCACCTGTGCCCAAACGCAAATGCGGAAACAACCCGCTT  -168

ZZA1  TTTGGATGATTATGCATTGTTCTCCACATTGTATGCTTCCAAGTTTCTGGTGGCAATACTG...ATACCCTAACGTTCATGATCAAAACTAATGTCTTC.....CCTACT  -56
      |||||||||||||||||||| |||||||||||||||||||||| ||||||||||||||||   |||||||||||||||||||||| | | ||| |||||
AOX1  TTTGGATGATTATGCATTGT.CTCCACATTGTATGCTTCCAAGATTCTGGTGGCAATACTGCTGATACCCTAACGTTCATGATCAAAATTTAACTGTTCTAACCCCTACT  -59
                                                      *
ZZA1  TGAACAG.CAATATATAAACAGAAC.AAGATTTCCTTTCTAACGTCTTTTTTTTTTATCATCATTATCAGCTTACTTTCATAATTGTGACTGGTTCCAATTGACAAGCTTT  53
       | ||||  |||||||||||||||  |  ||| ||   |||||||||||||| ||||||||||||||| || |||||||||||||| ||||||||||||||||||||||
AOX1  TGGACAGCCAATATATAAACAGAACGAACCTGCCCTGTCTTAAACCTTTTTTTTTATCATCATTATTAGCTTACTTTCATAATTGCGACTGGTTCCAATTGACAAGCTTT  52

ZZA1  TGATTCTAACGACTTT.AACGACAACCTAAAGAAC...AAAAACAACTAATTATTCGAAACAATGGCTATTCCCGAAGAATTTGATATTATCGTCTGTGGTGGTGGATCC  159
      ||||| ||||||||||  |||  ||||||| ||      |||||||||||||||||  ||||||||||||||||||||| |||||||||| |||||| || |||||||||
AOX1  TGATTTTAACGACTTTTAACGACAACTTGAGAAGATCAAAAAACAACTAATTATTCGAAACGATGGCTATCCCCGAAGAGTTTGATATCCTAGTTCTAGGTGGTGGATCC  162
```

FIG.10

```
ZZA1(P)  -316   TCAAAAAGAAACTTCCAATGTCGGCATA
AOX1(P)  -314   TCAAAAAGAAACTTCCAAAAGTCGCCATA

ZZA1(P)  -141   ACATTGTATGCTTCCAAGTTTCTGGTGG
AOX1(P)  -140   ACATTGTATGCTTCCAAGATTCTGGTGG
AOX2(P)  -275   ACAGTTGGGAGTTTCCAATTGGTTGGTTTT
MOX (H)  -409   TGTGCTGGATGC.ACCAATTAATTGTTGC
MOX (H)  -658   GGCTTTGGTCATTT.CAATGTTGTCGTC
AOD (C)  -583   AAAATGCTCTTTTCCATCATCATCATC
DAS (H)  -751   GTCTTTGATGTCTTCCA.CCATCTGCAGAT

Consensus       TTG.....TTCCAA.....TGGT

ZZA1(P)  +35    AATTGTGACTGGTTCCAATTGACAAGCTT
AOX1(P)  +25    AATTGCGACTGGTTCCAATTGACAAGCTT
MOX (H)  -61    AATTCT.TATGCTACCGTGCAGCGACTC
DAS (H)  -96    AATTTAGCCTCGTTCCAGCCATTCACGG

Consensus       AATT..G.CTGGTTCCA.......A.

ZZA1(P)  -160   ACACCCGCTTTTTGG
AOX1(P)  -169   CAACCCGCTTTTTGG
AOX2(P)  -127   AAAACCCCTTTTATG
MOX (H)  -24    ATCCCCAGTTTTTGC
AOD (C)  -694   AATTACTCTTTTGG
DAS (H)  -251   CGCAAGCCTTTTTGC

Consensus       CC.CTTTTTG
```

```
ZZA2T  GAAAAGGCTCCCACTCTGGGTGGTGAAGACTTAGGATACTCTGGGTGATG   50
       ||||||  ||  ||||  |||   ||||||||||||||||||  |  |||  |
AOX2   GAAAAGACTGCCACCTTGGTTGGTGAAGACTTAGGATACACAGG.TGANG
       ||||||||||||||| ||||||||| |||||  ||||||||||| | |||  |
AOX1   GAAAAGACTGCCACTTTGGTTGGAGAAGATTTAGGATACTCTGG.TGANG
       GluLysThrAlaThrLeuValGlyGluAspLeuGlyTyrSerGly GluA

ZZA2T  CCCTGGACATGACTGTTCCTCAGTTCAAGTTGGGAACTTACGAGAAGACT   100
       ||  |  |||||||||||  ||||||||||||||||| ||||||||||||||
AOX2   CCTTAGACATGACTGTACCTCAGTTCAAGTTGGGCACTTACGAGAAGACT
       |||||||||||||||| |||||||||||||||||||||||||||||||||
AOX1   CCTTAGACATGACTGTTCCTCAGTTCAAGTTGGGCACTTACGAGAAGACC
       laLeuAspMetThrValProGlnPheLysLeuGlyThrTyrGluLysThr

ZZA2T  GGTCTTGCTAGATTCTAGTTTGTTCTGTCnnCGAATATTTTTTAAATGA   150
       |||||||||||||||||||||||  |||        ||  ||||||  |
AOX2   GGTCTTGCTAGATTCTAGTTTATGTTGTATCTATGAATATTTTTTTACAT
       ||||||||||||| |      ||  ||          |||          |
AOX1   GGTCTTGCTAGATTCTAATCAAGAGGATGTCAGAATGCCATTTGCCTGAG
       GlyLeuAlaArgPheEnd

ZZA2T  TTGATTTTTCCTGTCAACATTGTTTAGTTATTTATGTCGTTATAGTCACT   200
              |||  |  ||   ||    |  || |||||||||||||||||
AOX2   GGTGGATTTGTTCCAATCTAGTTGTTAGTTATT.TGTCGTTATAGTCACT
         |   |||  || | |  |||||      ||||         ||||  |
AOX1   AGATGCAGGCTTCATTTTTGATACTTTTTTATTTGTAACCTATATAGTAT

ZZA2T  AAnACAGTTTAGCTTCTTnGGAATTTTTTCTCTCGTACCACACAG.....   245
       || ||||||       |        || ||  | ||       |
AOX2   AATACAGTTACCATCGGAATCTTTTCATTTCTTTTTTATACGTACGTATAT
        |  |  ||    ||   |  ||||   ||  |          |||
AOX1   AGGATTTTTTTTGTCATTTTGTTTCTTCTCGTACGAGCTTGCTCCTGATC
                                      ||||  || | || |  ||||| || |||
ZZA1T                                 TTCTCCTGGCACTATTTTGCTTCTTATC

ZZA2T  ATACTAGAnnTAGAATGCACCCACAGCGACTAATAnCAACGGAGCTTGAT   295
       |||||||    |||||||   ||   |||  || | ||  ||  ||||||
AOX2   GTACTAGATGAAGAATGCGACAAGGCCGACCAACAGCAATGGTGCTTGGT
        |||  |    ||   |     |         |   |||
AOX1   AGCCTATCTCGCAGCTGATGAATATCTTGTGGTAGGGGTTTGGGAAAATC
       ||  ||||||      ||  ||  |||||||||||| |   |||  ||||||||||
ZZA1T  AGTCTATCTTTGAGTTGGTGAATATCTTGAGACATGGGCTTGGGGAAAATC

ZZA2T  ACCnCAGGTTAGGAGGTGCTACGGAATTGnCCCATGATATCTCCGTAGAG   345
       |||   ||  ||||||||||||||||||| ||  |||||   ||  |||
AOX2   ACCAAAGTTTGGAAGGTGCTACCGAATTGGCCGATGATATTGAAGTGGAG
          |  ||||||       |||  ||   |   ||||
AOX1   ATTCGAGTTTGATGTTTTTCTTGGTATTTCCCACTCCTCTTCAGAGTACA
       |||  ||  ||  ||||||  |||||||||  ||  || | ||||| ||||  |
ZZA1T  ATTTGATTTCGAAGTTTTGCTTGGTAGTTGACATTCTTCTTCGGAGTATA
```

PICHIA PASTORIS ALCOHOL OXIDASE ZZA1 AND ZZA2 REGULATORY REGIONS FOR HETEROLOGOUS GENE EXPRESSION

RELATED APPLICATION

This patent application is a continuation-in-part of U.S patent application 08/037,618 filed Mar. 5, 1993 abandoned and a continuation-in-part of U.S patent application 08/037,617 filed Mar. 25, 1993, abandoned.

FIELD OF THE INVENTION

This invention relates to the field of recombinant DNA technology. More specifically, the invention relates to isolated proteins and nucleic acid sequences from methylotrophic yeast cells and the production of ethanol using α-amylase.

BACKGROUND

There has been an intense interest in the structure and function of the regulatory regions controlling the expression of genes in the pathway for methanol utilization. The methylotrophic yeasts are found in four genera that can be divided into two groups the ascosporogenous Hansenula and Pichia, and the asporogenous Candida and Torulopsis. The first enzyme in the methanol-utilization pathway is alcohol oxidase. It catalyzes the oxidation of methanol to formaldehyde. During this reaction there is a simultaneous reduction of oxygen to hydrogen peroxide. When glucose grown yeast cells are transferred to methanol containing media as a sole carbon source, the peroxisome, a subcellular organelle, begins to swell and proliferate. Large amounts of alcohol oxidase are sequestered into the peroxisomes. The compartmentalization of alcohol oxidase in the peroxisomes protects the cytosol from hydrogen peroxide. The high concentration of this enzyme compensates for its low affinity for oxygen. In methanol-grown Pichia pastoris cells, alcohol oxidase constitutes up to 30% of the total soluble protein.

Alcohol oxidases have numerous commercial applications. These uses include the measurement of alcohol levels in various biological and nonbiological fluids, and the conversion of alcohol precursor molecules into aldehydes, e.g., for use in artificial flavor production.

Several genes encoding alcohol oxidase from Pichia pastoris (AOX1, AOX2), Candida boidinii S2 (AOD1), and methanol oxidase from Hansenula polymorpha (MOX1) have been isolated and characterized. The regulation of the synthesis of alcohol oxidase is primarily controlled at the level of transcription. During methanol induction, the rapid de novo synthesis of the enzyme is accompanied by a dramatic increase in alcohol oxidase mRNA. Previous studies by Ellis et al., Mol. Cell. Biol, 5: 1111–1121 (1985) of the AOX1 promoter indicates that it is strongly repressed by ethanol and glucose. Based on northern hybridizations, Pichia pastoris cells grown in the presence of ethanol did not synthesize alcohol oxidase specific poly(A)$^+$ RNA. The synthesis of alcohol oxidase is tightly catabolite repressed. In cells grown in glucose containing media, alcohol oxidase mRNA is not detectable. In order to study the regulation of the AOX1 gene Tschopp et al., Nucl. Acids Res., 15: 3859–3876 (1987) took the AOX1 promoter and fused it to the E. coli lacZ gene. Saccharomyces cerevisiae strains harboring an AOX1-lacZ fusion produced only small amounts of active enzyme when grown in glucose or ethanol. See Stroman et al., U.S. Pat. No. 4,855,231.

The methylotrophic yeasts Hansenula polymorpha and Pichia pastoris have been used as hosts for heterologous gene expression. Cregg et al., Bio/Technology, 5: 479–485 (1987); Tschopp et al., Bio/Technology, 5: 1305–1308 (1987). Over twenty proteins of potential commercial value have been produced using methanol regulated promoters. These heterologous proteins can accumulate to high levels in the cytoplasm (tumor necrosis factor was expressed at 8 g/liter, Skeekrishna et al., Biochemistry, 28: 4117–4125, 1989) or can be secreted into the media (Saccharomyces cerevisiae invertase was secreted at 2.5 g/liter, Tschopp et al., Bio/Technology, 5: 1305–1308, 1987). Stable transformants have been obtained by integrating the alcohol oxidase promoter expression cassette into the yeast chromosomes. Increases in the level of expression have been obtained by increasing the number of integrated copies of the heterologous gene expression cassette (tetanus toxin fragment C was expressed at 12 g/liter, Clare et al., Bio/Technology, 9: 455–460).

Methylotrophic yeasts have been used in the production of heterologous proteins. Increases in gene dosage, cell density, and promoter strength have resulted in high-level expression of valuable proteins. Several genes encoding alcohol oxidase (Pichia pastoris AOX1, AOX2, and Candida Boidinii S2 AOD1), methanol oxidase (Hansenula polymorpha MOX), and dihydroxyacetone synthase (Hansenula polymorpha DHAS) have been isolated and characterized, see, for example, Ellis et al., Mol. Cell. Biol, 5: 1111–1121 (1985) (AOX1); Koutz et al., Yeast, 5: 167–177 (1989) (AOX2); Sakai et al., Gene, 114: 67–73 (1992) (AOD1); Ledeboer et al., Nucl. Acids Res., 13: 3063–3082 (1985) (MOX1). The synthesis of these enzymes is tightly controlled by methanol induction and glucose catabolite repression. When Pichia pastoris is grown on methanol as a sole carbon source, alcohol oxidase (a peroxisomal packaged enzyme) constitutes up to 30% of the total soluble protein.

Although high-level expression of heterologous proteins has been achieved using some methylotrophic yeast promoters, very little is known about the molecular mechanism involved in methanol induction. Previous studies comparing the methanol regulated promoters did not reveal any significant regions of homology. Koutz et al., Yeast, 5: 167–177 (1989); Sakai et al., Gene, 114: 67–73 (1992); Ledeboer et al., Nucl. Acids Res., 13: 3063–3082 (1985). A possible mechanism for the methanol induction of the methanol regulated gene is by means of a positive effector molecule that activates transcription by binding at specific DNA sequences, e.g., gene regulatory proteins. Thus, it is of interest to identify nucleotide sequences that are conserved among methanol regulated genes so as to identify molecules involved in their expression and regulation, and to confer similar forms of regulation on heterologous genes.

Given the recognized utility of methylotrophic yeast, as well as other yeast, in the expression of heterologous proteins, it is of interest to provide promoters and other regulatory nucleotide sequences for the controlled and/or high level expression of heterologous proteins in yeast. It is also of interest to identify new methanol regulated genes so as to provide for the increased production of the proteins encoded by these methanol regulated genes and to provide for nucleotide sequences involved in the expression of methanol regulated genes.

The breakdown of starch is an important process in the brewing, baking, and sweetener industries. The degradation of the starchy cereal grain endosperm is initiated by α-amylase. In rice (Oryza sativa), α-amylase is a monomeric Ca$_{2+}$-requiring metalloprotein which catalyzes an α(1–4) endoglycolytic cleavage of amylose and amylopectin. Since the yeast *Saccharomyces cerevisiae* which is commonly used in industry lacks the genes encoding for α-amylase, it is unable to directly ferment starch. During the commercial production of alcoholic beverages the starch is initially pretreated with an exogenous source of α-amylase.

Although the expression of a wheat α-amylase in yeast has been reported previously (Rothstein et al., *Gene*, 55: 353–356, 1987), the secretion of this protein across the cell membrane was minimal. Because the wheat a-amylase gene used is their study did not encode an enzyme containing an N-glycosylation site, the low level of secretion may by due to the lack of N-glycosylation. The secretion of barley α-amylase in yeast had higher levels of expression (Sogaard et al., *Gene*, 94: 173–179, 1990). The highest yield was 2–3 μg/ml of barley α-amylase AMY1 under the control of the 3'-phosphoglycerate kinase promoter. It is interesting to note that the rice α-amylase is the only cereal amylase known to be glycosylated. Kumagai, et al., *Gene*, 94: 209–216 (1990) expressed α-amylase OS103 (O'Neill et al., *Mol. Gen. Genet.*, 221: 235–244, 1990) in a laboratory strain of *Saccharomyces cerevisiae* under the transcriptional control of the enolase promoter. In that study, during the biosynthesis of rice α-amylase by yeast, the plant signal peptide was removed, the protein was N-glycosylated, and the active, enzyme was secreted into the culture media. Since the laboratory strain of *Saccharomyces cerevisiae* (LL20) used in that study was deficient in the enzyme maltase the recombinant strain LL20 [pEno/1031 is unable to produce significant amounts of ethanol. The reported yield of secreted enzyme was 1.8 μg/ml of rice α-amylase OS103.

Other amylolytic genes have been expressed in *Saccharomyces cerevisiae* cDNAs encoding mouse (Thomsen, *Carlsberg Res. Commun.*, 48: 545–555, 1983; Filho et al., *Bio/Technology*, 4: 311–315, 1986) and human salivary gland α-amylase (Sato et al., *Gene*, 50: 245–247, 1986), and *Aspergillus awamori* (Innis et al., *Science*, 228: 21–26, 1985) are some of the previous examples. Inlow et al., *Biotechnology and Bioengineering*, 32: 227–234, (1988) were able to convert Maltrin 150 (Grain Processing Corporation, Mucatin, IA) to ethanol. Maltrin 150 is a soluble starch which is enzymatically hydrolyzed by α-amylase.

Alcohol oxidases have numerous commercial applications. These uses include the measurement of alcohol levels in various biological and non-biological fluids, and the conversion of alcohol precursor molecules into aldehydes, e.g., for use in artificial flavor production.

Previous studies by Ellis et al., *Mol. Cell. Biol*, 5: 1111–1121 (1985) of the AOX1 promoter indicates that it is strongly repressed by ethanol and glucose. Based on Northern hybridizations, *Pichia pastoris* cells grown in the presence of ethanol did not synthesize alcohol oxidase specific poly(A)$^+$ RNA. In order to study the regulation of the AOX1 gene Tschopp et al., *Nucl. Acids Res.*, 15: 3859–3876 (1987) took the AOX1 promoter and fused it to the *E. coli* lacZ gene. *Saccharomyces cerevisiae* strains harboring an AOX1-lacZ fusion produced only small amounts of active enzyme when grown in glucose or ethanol. See Stroman et al., U.S. Pat. No. 4,855,231. This result indicates that the AOX1 promoter would not be useful in the production of heterologous proteins during ethanol production in *Saccharomyces cerevisiae*.

The subject invention provides for alcohol oxidase promoters that can direct high level expression of rice α-amylase in the brewer's yeast *Saccharomyces cerevisiae* and in other yeast species. The ZZA1 regulatory region contains several nucleotide sequences involved in promoter activity. These sequences include a TATAA box, located 45 bp upstream of the putative transcription initiation site. In order to find additional regulatory sites, the nucleotide sequence of ZZA1 promoter was compared to AOX1, AOX2, MOX1, AOD1, and DHAS genes. The highly conserved regions between these genes may be involved in binding methanol specific transacting factors. A region in the core consensus sequence of ZZA1 (GCTTCCA, position –123) is identical to the sequence which is adjacent the *S. cerevisiae* regulatory activating protein (RAPL) binding site, as noted in Buchanan et al., *Mol. Cell. Biol.*, 8: 210225, Brindle et al., *Mol. Cell. Biol.*, 10: 4872–4885. Deletion of the terminal G of the GCTTCCA sequence causes a loss in ENO1 gene expression. The CTTCC motif may also serve as a binding site for the trans-acting factor GCR1. This regulatory protein is required for high-level expression of several glycolytic genes in *S. cerevisiae* Huie, et al. *Mol. Cell. Biol.*, 12: 26900–2700 (1992).

SUMMARY OF THE INVENTION

An aspect of the invention is to provide isolated nucleotide sequences encoding the alcohol oxidases ZZA1 and ZZA2, and to provide the purified alcohol oxidases themselves. Another aspect of the subject invention is to provide for nucleotide sequences comprising the promoters and/or other portions of the ZZA1 and ZZA2 regulatory regions. Yet another aspect of the subject invention is to provide genetic constructions for the expression of heterologous genes using nucleotide sequences derived from the regulatory regions of ZZA1 and ZZA2. Another aspect of the invention is to provide host cells for the expression of heterologous proteins, in which the expression of the heterologous proteins is driven by promoters from the ZZA1 and ZZA2 regulatory regions. It is of particular interest to provide for *S. cereviase* cells expressing the heterologous protein rice α-amylase (gene OS 103) under the control of the ZZA1 promoter so as to be able to be grown in culture that can convert starch to ethanol.

Another aspect of the invention is to provide the nucleotide sequence (TTG-N3-GCTTCCAA-N5-TGGT) (SEQ ID NO:2) and the use of the nucleotide sequence. This nucleotide sequence is shown to be conserved and was found in the 5' flanking regions of alcohol oxidase, methanol oxidase, and dihydroxyacetone synthase genes in *Pichia pastoris*, *Hansenula polymorphs*, and *Candida Boidinii* S2.

It is also an aspect of the subject invention to provide for methods of isolating genes encoding proteins that modulate the expression of genes encoding proteins that modulate the expression of genes under the regulatory control of alcohol oxidase gene regulatory sequences, i.e., AOER (alcohol oxidase expression regulator) genes. Another aspect of the invention is to provide isolated AOER genes and purified AOER proteins.

One aspect of the subject invention is to provide methods for the conversion of starch into ethanol by culturing α-amylase secreting yeast cells in strach containing media.

BRIEF DESCRIPTION OF THE DRAWINGS

FIG. 5 is a sequence comparison between the 3' noncoding region of the ZZA1, AOX1, and AOX2 genes. The portion of ZZA1 in FIG. 5A and 5B is SEQ ID NO:26. The portion of AOX1 in FIG. 5A is SEQ ID NO:27. The portion of AOX2 in FIG. 5B is SEQ ID NO:28.

FIG. 9 is a partial nucleotide sequence (SEQ ID NO:1) of alcohol oxidase genomic clone ZZA1. The amino acid sequence of the ZZA1 encoded *Pichia pastoris* alcohol oxidase was determined from the nucleotide sequence of ZZA1. The restriction endonuclease sites are in bold and the putative transcription start point (+1) is marked with an asterisk. The putative TATA box is underlined.

FIG. 10 is the nucleotide sequence comparisons of *Pichia pastoris* ZZA1 and AOX1 alcohol oxidase 5'-flanking regions. The nucleotide sequences are aligned to maximize sequence similarity. The transcription start point (+1) is marked with an asterisk. Gaps, as indicated by (.), have been inserted to maximize sequence similarity. ZZA1 in FIG. 10 is SEQ ID NO:29. AOX1 in FIG. 10 is SEQ ID NO:30.

FIG. 11 is the sequence alignment of the TTCCAA and pyrimidine boxes of 6 methanol regulated genes from methylotrophic yeasts. The distance from the transcriptional start site to the first T of the consensus sequence is indicated as a negative number. P=*Pichia pastoris*, H=*Hansenula polymorpha*, C=*Candida boidinii* S2. ZZA1(P) –316 is SEQ ID NO:31. AOX1(P) –314 is SEQ ID NO:32. ZZA1(P) –141 is SEQ ID NO:33. AOX1(P) –140 is SEQ ID NO:34. AOX2(P) –275 is SEQ ID NO:35. MOX(H) –409 is SEQ ID NO:36. MOX(H) –658 is SEQ ID N0:37. AOD (C) –583 is SEQ ID NO:38. DAS(H) –751 is SEQ ID NO:39. The first consensus sequence is SEQ ID NO:40. ZZA1(P)+35 is SEQ ID NO:41. AOX1(P)+25 is SEQ ID NO:42. MOX(H) –61 is SEQ ID NO:43. DAS(H) –96 is SEQ ID NO:44. The second consensus seguence is SEQ ID NO:45. ZZA1(P) –160 is SEQ ID NO:46. AOX1(P) –169 is SEQ ID NO:47. AOX2 (P) –127 is SEQ ID NO:48. MOX(H) –24 is SEQ ID NO:49. AOD(C) –694 is SEQ ID NO:50. DAS(H) –251 is SEQ ID NO:51. The third consensus sequence is SEQ ID NO:52.

FIG. 18 is the nucleotide sequence comparisons of *Pichia pastoris* ZZA2, ZZA1, AOX1, and AOX2 alcohol oxidase 3'-terminal regionss. The portion of AAZ2 is (SEQ ID NO:53), ZZA1 is (SEQ ID NO:57), AOX1 are (SEQ ID NOS:55 and 56), and AOX2 is (SEQ ID NO:54). The nucleotide sequences are aligned to maximize sequence similarity. The transcription start point (+1) is marked with an asterisk. Gaps, as indicated by (.), have been inserted to maximize sequence similarity.

DETAILED DESCRIPTION OF THE SPECIFIC EMBODIMENTS

Definitions

Figure 15:
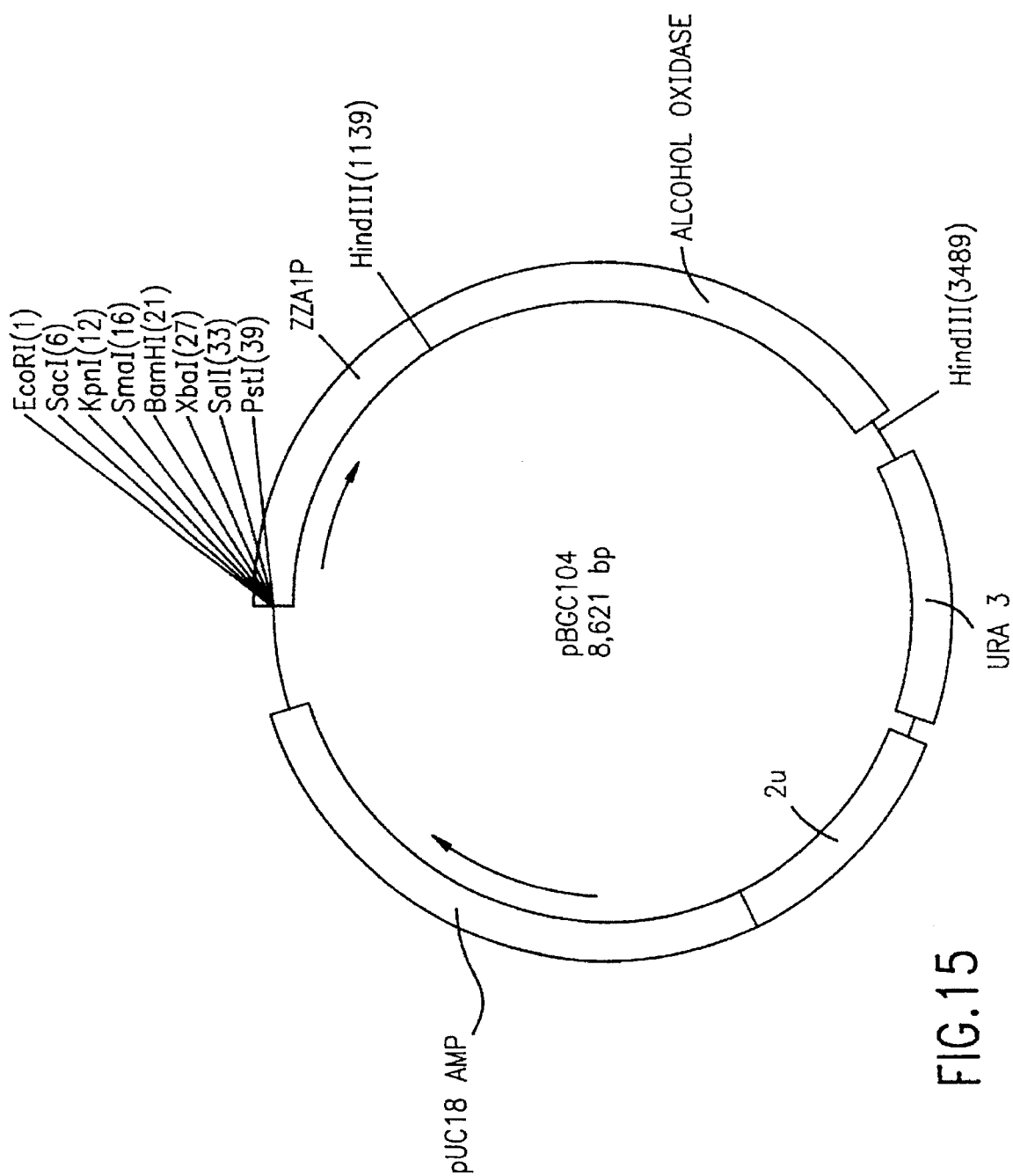
FIG. 15 is a map of the plasmid pBGC104.

The terms "ZZA1" and "ZZA2" as used herein refers to two alcohol oxidases. The genes encoding ZZA1 and ZZA2 are referred to by the terms "ZZA1" and "ZZA2", respectively. ZZA1 has a 5' non-coding region nucleotide sequence and N-terminal amino acid sequence as indicated in FIG. 9 (SEQ ID NO:1). The ZZA1 is at least partially encoded on plasmid pBGC104 (FIG. 15). ZZA2 may be identified as the gene at least partially encoded by the nucleotide sequence that is the insert in plasmid KS+ZZA2T, i.e., the amplification product of a PCR reaction performed on genomic DNA from *P. pastoris*, (obtained from Dr. H. Phaff, University of California, Davis (University ID #72-1033) ) using 24-mer oligonucleotide 5' TCG ACC CAG GTT TCA TGA ACG ATG 3'(SEQ ID NO:4) and the 31-mer oligonucleotide (5' TCC TGC AGC AAC CAA TGA GGA GAA TGA CAA C 3' (SEQ ID NO:5) as primers.

The term "gene", as used herein, refers not only to the nucleotide sequence encoding a specific protein, but also to any adjacent 5' and 3' non-coding nucleotide sequence involved in the regulation of expression of the protein encoded by the gene of interest. These non-coding sequences include terminator sequences, promoter sequences, upstream activator sequences, regulatory protein binding sequences, and the like. These non-coding sequence gene regions may be readily identified by comparison with previously identified eukaryotic non-coding sequence gene regions. Furthermore, the person of average skill in the art of molecular biology is able to identify the nucleotide sequences forming the non-coding regions of a gene using well-known techniques such as a site-directed mutagenesis, sequential deletion, promoter probe vectors, and the like.

The term "regulatory region" or "regulatory sequence" as used herein in reference to a specific gene refers to the non-coding nucleotide sequences within that gene that are necessary or sufficient to provide for the regulated expression of the coding region of a gene. Thus the term regulatory region includes promoter sequences, regulatory protein binding sites, upstream activator sequences, and the like. Specific nucleotides within a regulatory region may serve multiple functions. For example, a specific nucleotide may be part of a promoter and participate in the binding of a transcriptional activator protein.

The term "coding region" as used herein refers to that portion of a gene which codes for a protein. The term "non-coding region" refers to that portion of a gene that is not a coding region.

The term "alcohol oxidase", as used herein refers to an enzyme able to catalyze the reaction $RCH_2OH+O_2$ =$RCHO+H_2O_2$ where R is hydrogen or a lower alkyl, generally selected from the group H—, $CH_3$—, $CH_3CH_2$—, and $CH_3 (CH_2)_2$—.

The term "operably linked" refers to a juxtaposition of components, particularly nucleotide sequences, such that the normal function of the components can be performed. Thus, a coding sequence "operably linked" to regulatory sequences refers to a configuration of nucleotide sequences wherein the coding sequences can be expressed under the regulatory control i.e., transcriptional and/or translational control, of the regulatory sequences.

By "purified" it is meant, when referring to a peptide of nucleotide sequence, that the indicated molecule is present in the substantial absence of other biological macromolecular, e.g., polypeptides, polynucleic acids, and the like of the same type. The term "purified" as used herein preferably means at least 95% by weight, more preferably at least 99.8% by weight, of biological macromolecules of the same type present (but water, buffers, and other small molecules, especially molecules having a molecular weight of less than 1000 can be present). The term "pure" as used herein preferably has the same numerical limits as "purified" immediately above.

The term "isolated" as used herein refers to a polypeptide, polynucleotide molecules separated not only from other peptides, DNAS, or RNAS, respectively, that are present in the natural source of the macromolecule but also from other macromolecules and preferably refers to a macromolecule found in the presence of (if anything) only a solvent, buffer, ion or other component normally present in a solution of the same. "Isolated" and "purified" do not encompass either natural materials in their native state or natural materials that have been separated into components (e.g., in an acrylamide gel) but not obtained either as pure substances or as solutions.

In representations of nucleotide sequences provided herein, the following conventions are used. N refers to a nucleotide sequence location that may be of any nucleotide base. Y refers to a nucleotide base that is a pyrimidine.

Salts of any of the macromolecules described herein, i.e., proteins and polynucleotide sequences, will naturally occur when such molecules are present in (or isolated from) aqueous solutions of various pHs. All salts of peptides and other macromolecules having the indicated biological activity are considered to be within the scope of the present invention. Examples include alkali, alkaline earth, and other metal salts of carboxylic acid residues, acid addition salts (e.g., HCl) of amino residues, and zwitterions formed by reactions between carboxylic acid and amino residues within the same molecule.

The degree of similarity between the nucleic acid sequences of two polynucleotides may be measured by determining whether the two polynucleotide sequences can hybridize to each other under a given set of conditions so as to form hybrid heterodimers between the two sequences. These hybridization conditions may be varied so that the hybridization interaction between the two polynucleotide sequences occurs at a certain number of degrees centigrade below the melting temperature, Tm, of the duplex polynucleotide molecule used as the hybridization probe. Tm is defined as the temperature at which half the duplex molecules have dissociated into their constituent single strands. The Tm for a given double stranded polynucleotide may be determined empirically or by reference to well-known formulas that take into account hybridization condition factors that influence Tm (including the types of nucleic acids used), e.g. for DNA-DNA hybridization probes longer than 50 nucleotides, Tm=81.5° C.+16.6 log M+41 (mole fraction G+C) −500/L −0.62 (% formamide) (M is the molar monovalent cation concentration), Berger and Kimmel, *Guide to Molecular Cloning Techniques, Methods in Enzymology*, Volume 152, Academic Press, San Diego, Calif. (1987). The stringency of a hybridization may be defined as degrees centigrade below the Tm at nucleotide sequence for comparison. The degree of stringency of hybridization is said to decrease as hybridization takes place at a temperature increasingly below the Tm of the hybridization probe. Maximum stringency typically occurs at about Tm-5° C., i.e., at a temperature 5° C. below the Tm of the hybridization probe. "High stringency,, hybridization is said to take place at a temperature of about 5°–10° C. below Tm. "Intermediate stringency" hybridization is said to take place at a temperature of about 10°–20° C. below Tm. "Low stringency hybridization", i.e., maximum hybridization, is said to take place at a temperature of about 20°–25° C. below Tm. Two polynucleic acid sequences that can hybridize to one another under high stringency conditions can also hybridize to one another under low stringency conditions. Two polynucleic acid sequences that can hybridize to one another under low stringency conditions cannot necessarily hybridize to one another under low stringency conditions.

THE INVENTION

The present invention provides for isolated nucleotide sequences encoding alcohol oxidase proteins ZZA1 and ZZA2 and provides for the isolated alcohol oxidases themselves. The present invention also provides for the non-coding nucleotide sequences that are part of the ZZA1 and ZZA2 genes and various genetic constructions employing these non-coding nucleotide sequences to direct the expression of heterologous proteins. Also provided for are methods of expressing heterologous proteins using the ZZA1 and ZZA2 regulatory sequences and cells for the expression of the heterologous proteins. The present invention also provides for methods of isolating genes encoding proteins that modulate the expression of genes under the regulatory control of alcohol oxidase gene regulatory sequences (AOER genes), AOER genes themselves, and proteins encoded by AOER proteins. Specifically described herein is the discovery of two previously unknown alcohol oxidases present in a naturally occurring *P. pastoris* strain (obtained from Dr. H. Phaff, University of California, Davis (University ID #72-1033)), ZZA1 and ZZA2, and the isolation of the genes encoding these newly discovered alcohol oxidases. The 5' non-coding region sequence of the ZZA1 gene is extensively analyzed and shown to possess regions of significant homology to the 5' non-coding regions of other methanol regulated genes isolated from methylotrophic yeast. The 5'-non-coding homology provided herein reveals a hitherto undescribed conserved sequence (TTGNNNGCTTCCANNNNNTGGT) (SEQ ID NO:2) present in the 51 regulatory region of methanol regulated genes present in methylothropic yeast. The ZZA1 regulatory regions containing the conserved sequence are demonstrated to confer catabolite repression on the expression of heterologous proteins. The ZZA1 regulatory regions containing the conserved sequence confers heterologous gene expression in the presence of ethanol; i.e., this promoter is not ethanol repressed. Adding additional copies of the conserved sequence TTCCAA to the 5' non-coding region of a heterologous gene is demonstrated to increase the expression levels of that gene.

The subject invention provides for two novel alcohol oxidases, ZZA1 and ZZA2. ZZA1 and ZZA2 can be seen to be distinct from the previously identified *P. pastoris* alcohol oxidases AOX1 and AOX2 because the primers used to isolate ZZA1 and ZZA2 would not be expected to amplify AOX1 and AOX2. Additionally, nucleotide sequence comparisons of ZZA1 and ZZA2 with AOX1 and AOX2 reveal that the genes (and consequently the proteins) are distinct from one another. The non-coding regions of the AOX1 and AOX2 genes have a different nucleotide sequence from corresponding regions of the ZZA1 gene. Additionally, partial sequence analysis of the predicted N-terminus of ZZA1 indicates that the protein is distinct from AOX1 and AOX2. The ZZA2 gene was obtained by performing PCR amplification on *P. pastoris* DNA using the primers (5' TCG ACC CAG GTT TCA TGA ACG ATG 3') (SEQ ID NO:4) and (5'TCC TGC AGC AAC CAA TGA GGA GAA TGA CAA C 3') (SEQ ID NO:5). The 910 bp fragment obtained from the PCR amplification was not expected based on the available sequence information of the AOX1, AOX2, or ZZA1 genes.

Although the complete nucleotide sequences of ZZA1 and ZZA2 are not explicitly provided herein, sufficient information is provided so as to enable the person of average skill in the art of molecular biology to obtain the complete nucleotide sequences by the use of routine molecular biology techniques. Similarly, the complete amino acid sequences of ZZA1 and ZZA2 are not explicitly provided; however, the information provided herein enables a person of average skill in the art to obtain the complete nucleotide sequence without undue experimentation. In other words ZZA1 and ZZA2 are described in sufficient detail, i.e. the PCR primers used for isolation and the nucleotide sequences of FIGS. 5, 9, and 10, to obtain the complete nucleotide sequence (and predicted encoded amino acid sequence) by applying routine molecular biology techniques, such as those described in *Molecular Cloning: A Laboratory Manual*, 2nd Ed., Sambrook et al., Cold Spring Harbor Press, Cold Spring Harbor, N.Y. (1989), e.g, the nucleotide sequence of cloned fragments may be completed by routine sequencing, and incompletely cloned sequences may be used as hybridization probes to obtain the remainder of the sequence.

Although ZZA1 and ZZA2 possess unique primary amino acid sequences, the subject invention also provides for numerous ZZA1 and ZZA2 "variants." These "variants" are proteins that have alcohol oxidase activity and possess primary amino acid sequences similar (but not identical), i.e., homologous, to the primary amino of ZZA1 and/or ZZA2. These ZZA1 and ZZA2 "variants" may have one or more amino acid substitutions. Preferably these substitutions are the result of the substitution of one amino acid with another amino acid that has a similar chemical structure, i.e., a conservative substitution. Examples of conservative substitution are the replacement of a leucine with an isoleucine or a valine, an aspartate with a glutamate, and a threonine with a serine. Furthermore, the ZZA1 and ZZA2 variants provided for include proteins with the primary amino acid sequence of ZZA1 and ZZA2, but possessing various minor amino acid deletions and/or insertions, typically in the range of about 1–5 amino acids, as well as one or more amino acid substitutions. Other ZZA1 and ZZA2 variants provided for include chimeric proteins produced by adding heterologous signal sequences.

By providing for the amino acid sequence of hitherto unknown alcohol oxidases, the subject invention greatly enhances the level of guidance available to the person of average skill in the art of molecular biology attempting to make biologically active variants of alcohol oxidases, including ZZA1 and ZZA2. The level of guidance is enhanced because knowledge of regions of homology between proteins of similar biological activity indicate where amino acid sequence changes can be made without abolishing biological activity, i.e., at the most variable regions.

In addition to providing for the nucleotide sequences of genes ZZA1 and ZZA2, the subject invention also provides for numerous nucleotide sequences bearing homology to nucleotide sequences of ZZA1 and ZZA2. Sequences of interest bearing homology to the nucleotide sequences encoding ZZA1 and ZZA2 include nucleotide sequences encoding ZZA1 and ZZA2 variants.

It will be appreciated by those skilled in the art that as a result of the degeneracy of the genetic code, a multitude of ZZA1 and ZZA2 encoding nucleotide sequences, some bearing minimal nucleotide sequence homology to the nucleotide sequences of ZZA1 and ZZA2, may be produced. The subject invention has specifically contemplated each and every possible variation of peptide or nucleotide sequence that could be made by selecting combinations based on the possible amino acid and codon choices made in accordance with the standard triplet genetic code as applied to the sequence of ZZA1 and ZZA2 and all such variations are to be considered as being specifically disclosed.

Although nucleotide sequences encoding ZZA1 and ZZA2 and variants thereof are preferably capable of hybridizing to the nucleotide sequences of ZZA1 and ZZA2, respectively, under stringent conditions, it may be advantageous to produce nucleotide sequences encoding ZZA1 and ZZA2 (or ZZA1 and ZZA2 variants) possessing a substantially different coding sequences. Codons can be selected for use in a particular expression host organism in accordance with the frequency with which a particular codon is utilized by the host to increase the rate at which expression of the peptide occurs. Other reasons for substantially altering the nucleotide sequence encoding a protein without altering the amino acid sequence include the production of RNA transcripts having more desirable properties, e.g., greater halflife, than transcripts produced from the sequence ZZA1 and ZZA2 and the like.

By providing for the nucleotide sequences of ZZA1 and ZZA2, the present invention enables numerous genetic manipulations of yeast, e.g., chromosomal insertions, gene inactivations, and the like, by employing well known yeast genetics techniques. These techniques may be applied to numerous yeast species, including, *S. cerevisiae* and *P. pastoris*. Description of suitable yeast genetic manipulation techniques can be found, among other places, in Guthrie, C., and Fink, G. R. *Methods in Enzymology, Volume 194: Yeast Genetics and Molecular Biology*, Academic Press, Inc., San Diego, Calif. (1991); Ito, H., Fukuda, Y., Murata, K., and Kimura, A. *J. Bacteriol.* 153: 163–168 (1983); Rodriguez, R. L., and Tait, R. C. *Recombinant DNA Techniques: An introduction*, Addison-Wesley, Reading, Mass. (1983); and Ausubel, F. M., Brent, R., Kingston, R. E., Moore, D. D., Seidmanz, J. G., Smith, J. A., and Struhl, K. *Current protocols in Molecular Biology. Volume II*, Greene Publishing Associates and Wiley-Interscience, New York, N.Y.

Nucleotide sequences of interest for joining to ZZA1, ZZA2, or fragments thereof, include numerous widely available cloning vectors, e.g., plasmids, cosmids, A phage derivatives, phasmids, and the like, that are in the public domain. Vectors of interest include expression vectors, replication vectors, hybridization probe generation vectors, sequencing vectors, and the like. In general, vectors of interest may contain an origin of replication functional in at least one organism, convenient restriction endonuclease digestion sites, and selectable markers for the host cell. Nucleotide sequences encoding ZZA1 and ZZA2 may be joined to a variety of other nucleotide sequences of interest by means of well established recombinant DNA techniques (see, for example, Sambrook, et al., *Molecular Cloning: A Laboratory Manual, 2nd Ed.*, Cold Spring Harbor (1989).

Expression vectors may be used to produce useful quantities of ZZA1 and ZZA2 in a variety of cell hosts. Detailed descriptions of many expression vectors and their use can be found, for example in Goeddel, *Gene Expression Technology Methods in Enzymology*, Vol. 185 Academic Press, San Diego, Calif. (1990). Expression vectors contain promoters functional in the host of interest. The promoter may be operably linked to the coding sequence of a gene of interest so as to produce a translatable mRNA transcript encoding ZZA1 and ZZA2. Expression vectors preferably have convenient restriction sites located near the promoter sequence so as to provide for the insertion of nucleic acid sequences encoding heterologous proteins. The promoters in suitable expression vectors may be either constitutive or inducible. In addition to having promoter sequences, expression vectors may contain various enhancer sequences and the like, included for the purpose of maximizing expression of ZZA1 and ZZA2.

ZZA1 and ZZA2 may be purified from a variety of cells. Suitable cell sources for the production of purified ZZA1 or ZZA2 include cells naturally producing these proteins, cells not naturally encoding ZZA1 or ZZA2, but genetically modified to do so, and cells naturally producing ZZA1 or ZZA2, but genetically modified so as to produce elevated levels of these proteins. Cells from which ZZA1 and ZZA2 may be isolated include both prokaryotic and eukaryotic cells. Preferred cellular sources for the isolation of variants are yeast cells genetically modified to overproduce ZZA1 or ZZA2, and naturally occurring strains of *Pichia Dastoris*.

It will be appreciated that an advantage of the subject invention is to apply recombinant DNA techniques so as to provide for cellular lysates that contain ZZA1 and/or ZZA2 in significantly higher, at least 2-fold, preferably at least 10-fold, higher concentrations than found in naturally occurring cells that have not been genetically modified. Since ZZA1 and ZZA2 variants are not naturally produced, it is apparent that cells from which these variants can be isolated do not naturally encode the variants, but are genetically modified to do so.

Numerous methods are known for purifying enzymes with alcohol oxidase activity. In general, routine variations of known methods for purifying alcohol oxidases may be used to purify ZZA1 and ZZA2. Methods for purifying alcohol oxidases have been described. Descriptions of these methods can be found, among other places, in U.S. Pat. No. 4,619,898, and Giuseppin et al., *Appl. Microbial. Biotechnol.* 28: 14–19 (1988)

The 5' non-coding region of ZZA1 contains nucleotide sequences known to be involved in the transcription and translation of eukaryotic genes (FIG. 9) (SEQ ID NO:1). At position −45, the sequence TATAAA formed a putative Goldberg-Hogness or TATA box The nucleotides flanking the first methionine codon (ATG, position+112) conformed to a preferred translation initiation sequence (ACCATGG) associated with many highly expressed eukaryotic mRNAs and the sequence CAAAAACAA (position +87–95) resembled the CA-rich nucleotides found 10–30 bp upstream of the translation initiation site in many *S. cerevisiae* genes. Two sequences TGGTTTG (position 31 631) and GGTTTG (position −361) were very similar to the animal core enhancer, $GTGG_{AAA}^{TTT}G$. (Laimens et al., pgs. 28–3, in *Enhancers and Eukaryotic Gene Expression: Current Communications in Molecular Biology*, Gluzman and Shenk eds., Cold Spring Harbor Press, Cold Spring Harbor, N.Y. (1983).

The nucleotide sequences of ZZA1 and AOX15' non-coding regions were compared, and the homology between the promoters was 64% (FIG. 10). Primer extension assays (see example 10) indicated that the transcription initiation site for ZZA1 is located 111 bp upstream of the start codon. This transcription initiation site is present in a highly conserved region, i.e., 39/40 nucleotides are identical between ZZA1 and AOX1.

Previous nucleotide sequence comparisons of methanol-regulated promoters from *Pichia pastoris* and *Hansenula polymorpha* failed to reveal any important regions of homology, see Ellis et al., *Mol. Cell. Biol.*, 5: 1111–1121, Koutz et al, *Yeast*, 5: 167–177, Ledeboer et al., *Nucl. Acids Res.*, 13: 3063–3082. The nucleotide sequence analysis provided herein identifies several conserved regions in methanol regulated genes (FIG. 11). A core motif consisting of the sequence TTCCAA occurred in three conserved regions in ZZA1 (−316, −120, +35). The TTCCAA core consensus sequence is surrounded by additional regions of homology that are spaced approximately ten base pairs apart, i.e., (TTGNNNNNTTCCAANNNNNTGGT (SEQ ID NO:6) and AATTNNNNNTGGTTCCANNNNNNNA (SEQ ID NO:7)). A pyrimidine box containing the conserved sequence CCYCTTTTG is present in ZZA1 at position −163. The TTCCAA and the pyrimidine boxes are present in all of the methanol-regulated genes analyzed.

There are several unique features in the ZZA1 51 upstream region which might be involved in controlling gene expression. The upstream region has two sequences TGGTTTG (position −631) and GGTTTG (position −361) which are very similar to the animal core enhancer, $GTG-G_{AAA}^{TTT}G$ and a putative alcohol dehydrogenase regulatory protein (ADR1) binding site GGAGA in a 30 bp imperfect palindrome GATGGATTCAGGAGAAATTGTTCTGC-CATC (SEQ ID NO:8) (−787). The ADR1 protein activates transcription of the catabolite repressed alcohol dehydrogenase 2 gene (ADH2) and acts as a positive regulator for the peroxisomal catalase A gene. The ZZA1 gene contains an upstream repression site (URS) GTTTCCTCAAGGCAA-GAACTCC (SEQ ID NO:3) (position −712) which shares homology to a URS in ENOI (GATTCCTCAAGGTATGCCTCTCC) (SEQ ID NO:9). Deletion of this site in ENO1 resulted in a 10-fold increase in gene expression in cells grown on glucose, as noted in Cohen et al., *Mol. Cell. Biol.*, 7: 2753–2761. Similarly, deleting the ZZA1 URS from the ZZA1 regulatory region increases the expression of genes under the control of the ZZA1 regulatory region and removes glucose repression control.

The subject invention provides for a novel conserved nucleotide sequence, TTGNNNGCTTC-CAANNNNNTGGT (SEQ ID No: 2), that may be used to increase the expression of genes of interest in a variety of cells. The conserved nucleotide sequence TTGNNNGCT-TCCAANNNNNTGGT (SEQ ID No: 2) is present in the 5' non-coding region of at least 6 methanol regulated genes from methylotrophic yeast. The conserved nucleotide sequence contains a consensus core sequence 5'-TTCCAA-3'. The addition of one or more copies of the TTCCAA consensus core sequence at locations proximate to the natural location of TTG-N3-GCTTCCAA-N5-TGGT, i.e., TTGNNNGCTTCCAANNNNNTGGT (SEQ ID NO:2) sequence, with respect to the transcription initiation site, may be used to increase the expression level of genes under the regulatory control of ZZA1 or ZZA2 regulatory sequences. The sequence TTGNNNGCTTC-CAANNNNNTGGT (SEQ ID NO:2) may also be used to confer some of the regulatory behavior of methanol regulated genes on heterologous proteins for expression. The regulatory regions of ZZA1, ZZA2, or portions thereof, may be operably linked to nucleotide sequences encoding heterologous protein i.e., heterologous with respect to the regulatory region, so as to place, at least in part, the expression of the heterologous protein under the regulation of the ZZA1 or ZZA2 regulatory sequences. The expression of a heterologous gene of interest may be driven by a promoter located within the ZZA1 or ZZA2 regulatory sequence. Also, by including a sufficient portion of ZZA1 or ZZA2 regulatory region nucleotide sequence in genetic constructions comprising the regulatory region, the expression heterologous genes of interest may be regulated similarly to the regulation of ZZA1, ZZA2, or other alcohol oxidase genes. Many heterologous proteins of interest may be expressed from nucleotide sequences under the regulatory control of ZZA1 or ZZA2 regulatory regions. These heterologous proteins include enzymes, hormones, short peptide, lymphokines, regulatory proteins, structural proteins, antigens (for use in inducing a specific immune response), and the like. Additionally, ZZA1 and ZZA2 regulatory regions may be used to control the transcription anti-sense RNA.

The promoter sequences within the ZZA1 and ZZA2 regulatory regions may be used to provide for the expression of heterologous and homologous proteins in a variety of cells, preferably eukaryotic cells. ZZA1 and ZZA2 promoters may be used to drive expression of genes in many cells from many species of yeast, including yeast species that are not methylotrophic, such as Saccharomyces and Kluvveromyces species. The high level of expression exhibited by the ZZA1 promoter in *S. cerevisiae* is of particular interest, given the substantial differences between *S. cerevisiae* cells and *P. pastoris* cells.

The subject invention provides for alcohol oxidase promoters that can direct high level expression of rice α-amylase in the brewer's yeast *Saccharomyces cerevisiae* and in other yeast species. The ZZA1 regulatory region contains several nucleotide sequences involved in promoter activity. These sequences include a TATAA box, located 45 bp upstream of the putative transcription initiation site. In order to find additional regulatory sites, the nucleotide sequence of ZZA1 promoter was compared to AOX1, AOX2, MOX1, AOD1, and DHAS genes. The highly conserved regions between these genes may be involved in binding methanol specific transacting factors. A region in the core consensus sequence of ZZA1 (GCTTCCA, position –123) is identical to the sequence which is adjacent the *S. cerevisiae* regulatory activating protein (RAPL) binding site, as noted in Buchanan et al., *Mol. Cell. Biol.*, 8: 210225, Brindle et al., *Mol. Cell. Biol.*, 10: 4872–4885. Deletion of the terminal G of the GCTTCCA sequence causes a loss in ENOI gene expression. The CTTCC motif may also serve as a binding site for the transacting factor GCR1. This regulatory protein is required for high-level expression of several glycolytic genes in *S. cerevisiae* Huie, et al. *Mol. Cell. Biol.*, 12: 26900–700 (1992).

Both AOX1 and AOX2 show differences in the levels of alcohol oxidase MRNA accumulation during methanol induction, Cregg et al., *Mol. Cell. Biol*, 9: 1316–1323. It is possible that differences in nucleotide sequence near the TTCCAA core consensus sequences might result in different binding efficiencies of positive regulatory proteins. Only AOX2 has a putative HAP2/HAP3 binding site (TGGTTGGT) next to the TTCCAA core consensus sequence, Olesen et al., *Cell*, 51: 953–961. The TGGTTGGT sequence acts as a upstream activator of the CYC1 gene, Hahn and Guarente. Science, 240: 317–321. Since the heme induced HAP2/HAP3 protein binds both CCAAT-boxes and TGGTTGGT elements, the AOX2 promoter might be regulated by heme (the relevant AOX2 sequences are TTCCAATTGGTTGGT (SEQ ID NO:10)). In *Saccharomyces cerevisiae* heme regulates the expression of catalase A, a peroxisomal enzyme.

Another aspect of the subject invention is to provide for methods of isolating genes encoding proteins that modulate the expression of genes under the regulatory control of alcohol oxidase gene regulatory regions. These genes under the regulatory control of alcohol oxidase gene regulatory regions are referred to as AOER (alcohol oxidase expression regulator) genes. The gene product of an AOER gene is referred to as an AOER protein. The subject invention provides for isolated AOER genes and purified AOER proteins.

The methods of isolating AOER genes provided for are based upon assays that detect interactions between AOER proteins and AOER protein binding sequences. Nucleotide sequences containing putative binding sites for AOER proteins to be used in AOER protein and gene isolation procedures may be derived from the regulatory region of ZZA1 or ZZA1, and preferably contain the conserved sequence TTGNNNGCTTCCAANNNNNNTGGT (SEQ ID NO:2). Numerous assays to detect interactions between gene expression regulatory proteins and target nucleotide binding sequences are known to the person of average skill in the art of molecular biology. These techniques are described, among other places, in *Molecular CloningA Laboratory Manual*, 2nd Ed., Sambrook et al., Cold Spring Harbor Press, Cold Spring Harbor, N.Y. (1989), *Guide to Molecular Cloning Technique: Methods in Enzymology Volume 152*, Berger and Kimmel, Academic Press, San Diego, Calif. (1990), and the like. Providing the information that a specific nucleotide sequence is a binding site for a protein that regulates gene expression enables the use of numerous well known methods for purifying proteins that bind to the specific nucleotide sequence and also enables the use of methods for isolating the genes encoding such gene regulatory proteins. These protein purification and gene isolation techniques may be conveniently applied to AOER proteins and genes encoding AOER proteins. Examples of such methods include the construction of fusions between putative regulatory protein binding nucleotide sequences and "reporter" genes encoding proteins conferring an easily detected phenotype, e.g., 9-galactosidase, α-amylase, and the like. When a genetic library containing an AOER encoding nucleotide sequence is moved into host cells containing reporter gene fusions, host cells containing library clones expressing proteins that modulate, i.e., increase or decrease, the expression of the reporter genes may readily be detected by means appropriate for the given reporter gene and host cell, e.g., blue colony color for *S. cerevisiae* cells containing a Lac Z. reporter and grown on X-gal containing media, halo formation in iodine stained starch media for *S. cerevisiae* containing an α-amylase reporter. Genetic libraries to be screened by the above-described screening assay are preferably prepared from nucleic acids isolated from an organism naturally encoding alcohol oxidase genes, more preferably a methylotrophic yeast, and even more preferably from *Pichia pastoris*.

AOER proteins may be purified using assays and/or separation techniques based on the ability of the proteins to specifically bind to nucleotide sequences within the regulatory regions of ZZA1 and ZZA2 genes. These techniques include gel mobility shift assays such as those described in Protein *Function: A Practical Approach*, Ed. Creighton, IRL Press, NY, N.Y. (1990). Other approaches for purifying AOER proteins include the technique of affinity chromatography using nucleotide sequences containing AOER binding sites. Affinity chromatography of DNA binding proteins is described, among other places, in the book *Guide to Protein Purification, Methods in Enzymology Vol.* 182, ed. Deutscher, Academic Press, San Diego, Calif. (1990).

Many well known cloning techniques may be used to isolate an AOER gene after AOER protein has been purified. The well known cloning techniques including, hybridization with oligonucleotide probes prepared on the basis of N-terminal sequence analysis of proteins, screening of expression libraries with antisera prepared against the protein of interest, PCR amplification using primers based on amino acid sequence analysis, and the like.

The invention having been described above, may be better understood by reference to the following examples. These examples are offered for the purpose of illustrating the subject invention, and should not be interpreted as limiting the invention.

EXAMPLES

Example 1

Pichia pastoris chromosomal DNA preparation

Yeast cells were grown in 30 mls of YEPD at 30° C. for 16 hours. The cells were pelleted using a table top centrifuge at 3,000 rpm for 5 minutes. The pellet was washed once in double distilled $H_2O$, once in 1M sorbitol, once in SED (SED is 1M Sorbitol, 25 mM EDTA, 50 mM DTT), and then resuspended in 5 ml of 0.1 M tris-HCL, pH 7.0, and 1 M sorbitol. The cells were mixed with 400 μl Zymolyase 100,000 (Seikagaku), 10 A1 of beta-mercaptoethanol and incubated at 30° C. for 1 hour. The resulting spheroplasts were then centrifuged at 1,000 g for 10 minutes and gently lysed with 4 ml of lysis buffer (0.1% SDS, 10 mM Tris-HCL, pH 7.4, 5 mM EDTA, 50 mM NaCl). 100 μl of Pronase (5 mg/ml, Boehringer Mannheim) and 100 ml RNase A (10 mg/ml, Sigma) were each added and the solution was incubated at 37° C. for 2 hours. The DNA was then extracted in 10 mls of chloroform containing isoamyl alcohol (24:1 v/v), and the phases were separated by centrifugation at 9,000 rpm for 10 minutes. The upper (aqueous) phase was transferred to a fresh tube and one volume of phenol/chloroform/isoamyl alcohol was added. The phases were separated by centrifugation (9,000 rpm for 15 minutes) and the upper (aqueous) phase was placed in a fresh tube. Two volumes of cold ethanol was added and the chromosomal DNA were spooled out using a glass rod. The DNA was then rinsed in 70% ethanol and immediately dissolved in 500 M1 of TE buffer.

Example 2

Southern hybridization with Pichia Pastoris genomic DNA Total chromosomal DNA was isolated as described in Example 1.6.6 Ag of total DNA was digested with the restriction endonucleases BamHI, PstI, EcoRI, and BglII and the DNA fragments were separated by 14 agarose gel electrophoresis. The DNA was then denatured, the gel was neutralized, and the DNA was transferred to nitrocellulose. The filters were then prehybridized at 42° C. for 16 hours in 5X SSPE, 5X Denhart's, 0.4 mg/ml denatured calf thymus DNA, 0.5% SDS. Hybridization was carried out at 42° C. for 16 hours in 5X SSPE, 5X Denhart's, 0.2 mg/ml denatured calf thymus DNA, 0.5% SDS. The $^{32}$P-labeled probe was prepared by annealing a 45-meroligonucleotide (5'CACCACCTAGAACTAGGATATCAAACTCTTCGG-GGATAGCCATCG3') (SEQ ID NO:11) to a 18-mer oligonucleotide (5'CGATGGCTATCCCCGAAG 3') (SEQ ID:12) and filling in the 27 base overhang with DATP, DGTP, dTTP, and ($\alpha$-$^{32}$P) dCTP. The labelled mixture was chromatographed on a Sephadex G-25 column. The labelled DNA fractions were pooled and boiled for 5 minutes and immediately added to the hybridization buffer. Hybridization was carried out at 42° C. for 18 hours. After hybridization the filters were washed twice for 15 minutes at room temperature in 5X SSPE, 0.2% SDS, and one time at 42° C. in iX SSPE, 0.2% SDS. The filters were then autoradiographed for 14 days.

Example 3

Construction of a partial Pichia pastoris genomic library.

Two micrograms of *Pichia pastoris* genomic DNA prepared as described in Example 1 were digested with PstI and BamHI. After fractionation by electrophoresis on a 1% low melt agarose gel, DNA fragments of approximately 1100 base pairs were isolated and subcloned into YEp352. This *Pichia pastoris* library was maintained in *Escherichia coli* strain C600. The transformed cells were plated on LB plates containing 100 μg/ml ampicillin. The plates were incubated at 37° C. for 24 hours and stored at 4° C. Approximately 500 independent transformants were transferred onto nitrocellulose and incubated for 12 hours on LB containing 200 μg/ml chloramphenicol. The colonies were then gently lysed by placing the filters on Whatman paper soaked in 1.5M NaCl and 0.5M NaOH for 5 minutes. The filters were then neutralized by transferring them to Whatman paper soaked in 1M Tris-HCL, pH 7.4 for 5 minutes and the transferred into holding buffer (1.5M NaCl, 0.5M Tris-HCL, pH 7.4). The filters were then dried at 650° C. for 2 hours.

Example 4

Colony hybridization

The nitrocellulose filters containing the partial genomic library prepared as described in Example 3 were prehybridized at 42° C. for 16 hours in 5X SSPE, 5X Denhart's, 0.4 mg/ml denatured calf thymus DNA, 0.5% SDS. Hybridization were carried out at 42° C. for 18 hours in 5X SSPE, 5X Denhart's, 0.4 mg/ml denatured calf thymus DNA, 0.5% SDS. The $^{32}$P-labeled probe was prepared by annealing a 45-meroligonucleotide (5'CACCACCTAGAACTAGGATATCAAACTCTTCGGG-GATAGCCATCG3') (SEQ ID NO:11) to a 18-mer oligonucleotide (5'CGATGGCTATCCCCGAAG 3') (SEQ ID NO:12) and filling in the 27 base overhang with dATP, dGTP, dTTP, and ($\alpha$-$^{32}$P) dCTP. The labelled mixture was chromatographed on a Sephadex G-25 column. The labelled DNA fractions were pooled and boiled for 5 minutes and immediately added to the hybridization buffer. After hybridization the filters were washed twice for 15 minutes at room temperature, and one time at 42° C. The filters were then autoradiographed for 3 days.

Example 5

Isolation of Alcohol Oxidase ZZA1 promoter

Figure 1:
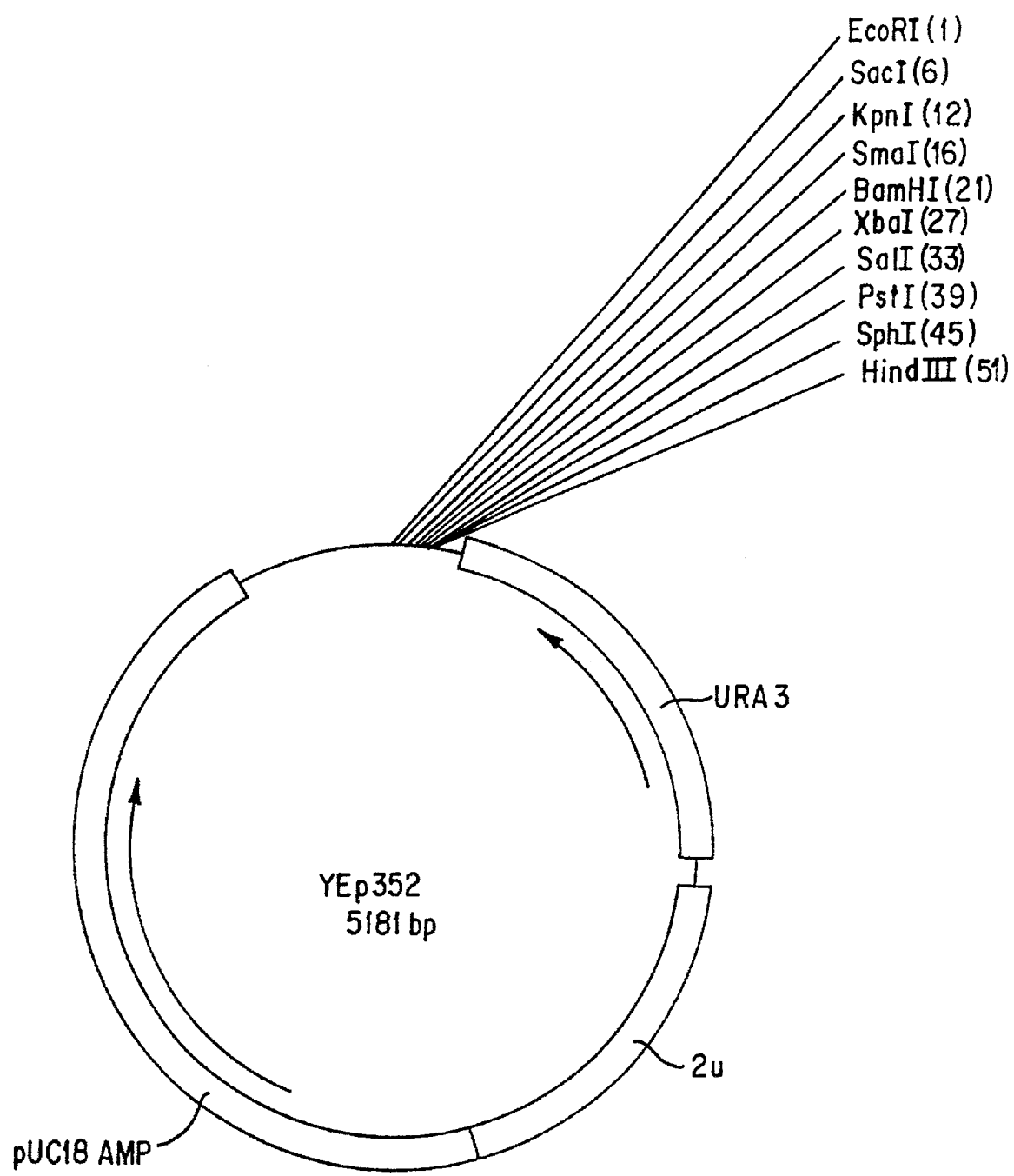
FIG. 1 is a map of the plasmid YEP 352.
Figure 2:
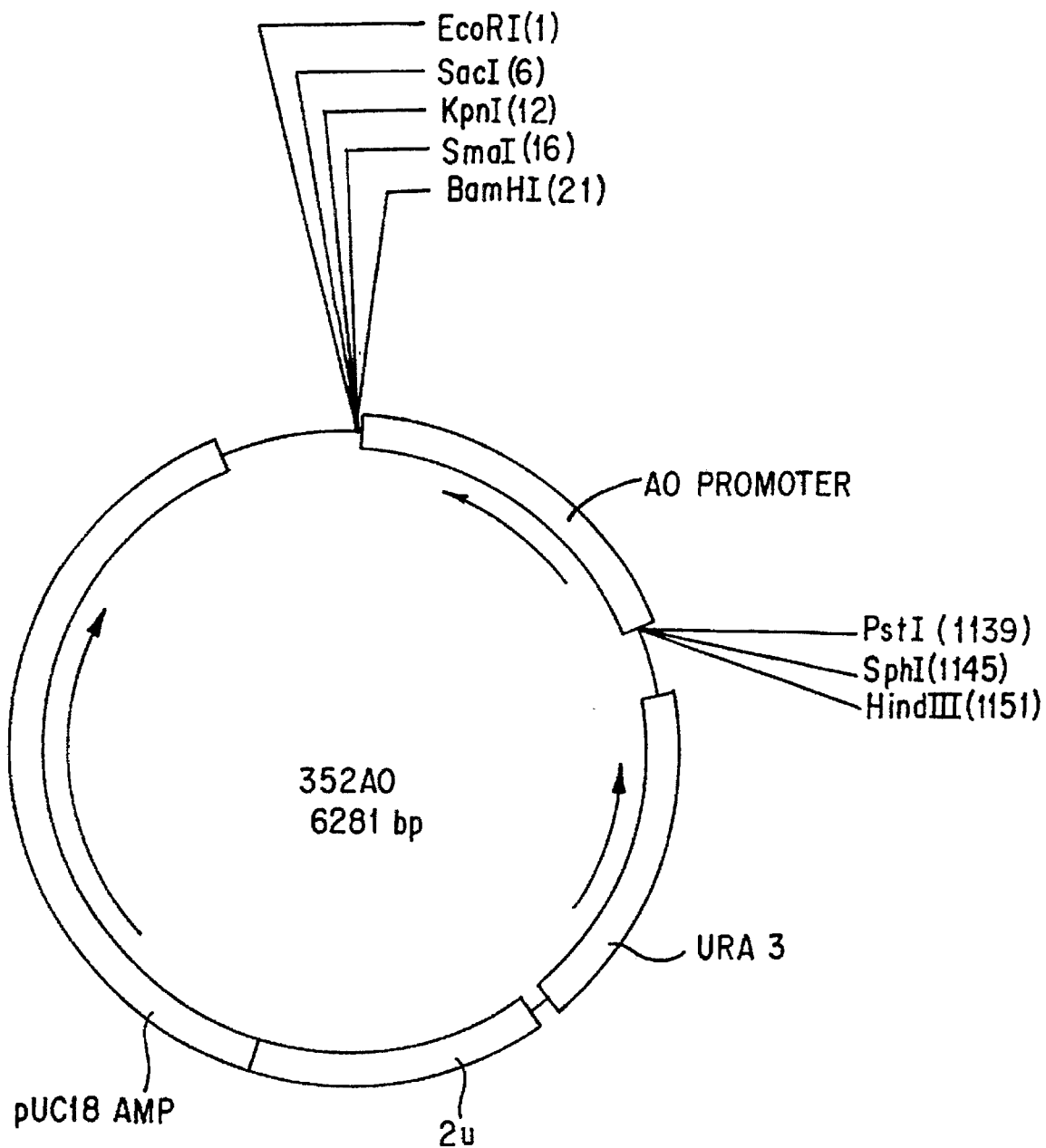
FIG. 2 is a plasmid map of the *E. coli*/yeast shuttle vector 352AO. This clone contains the 5' regulatory region of the ZZA1 gene and a portion of the protein ZZA1 structural gene.

Two micrograms of Pichia pastoris genomic DNA were digested with PstI and BamHI. After fractionation by electrophoresis on a 1% low melt agarose gel DNA fragments of approximately 1100 base pairs were isolated and subcloned into YEp352 (FIG. 1) This *Pichia pastoris* library was maintained in *Escherichia coli* strain C600. Approximately 500 independent transformants were screened by colony hybridization using a $^{32}$P-labeled probe prepared by annealing a 45-mer oligonucleotide (5'CACCACCTAGAACTAGGATATCAAACTCTTCGG-GGATAGCCATCG 3') (SEQ ID NO:11) to a 18-mer oligonucleotide (5'CGATGGCTATCCCCGAAG 3')(SEQ ID NO:12) and filling in the 27 base overhang with dATP, dGTP, dTTP, and ($\alpha$-$^{32}$P) DCTP. Hybridizations were carried out at 42° C. for 16 hours in 5X SSPE. 5X Denhart's, 0.2 mg/ml denatured calf thymus DNA, 0.5% SDS. A putative alcohol oxidase genomic clone 352 AO (FIG. 2) was identified and characterized by restriction mapping.

Example 6

Isolation of Alcohol Oxidase ZZA1 gene.

Figure 4:
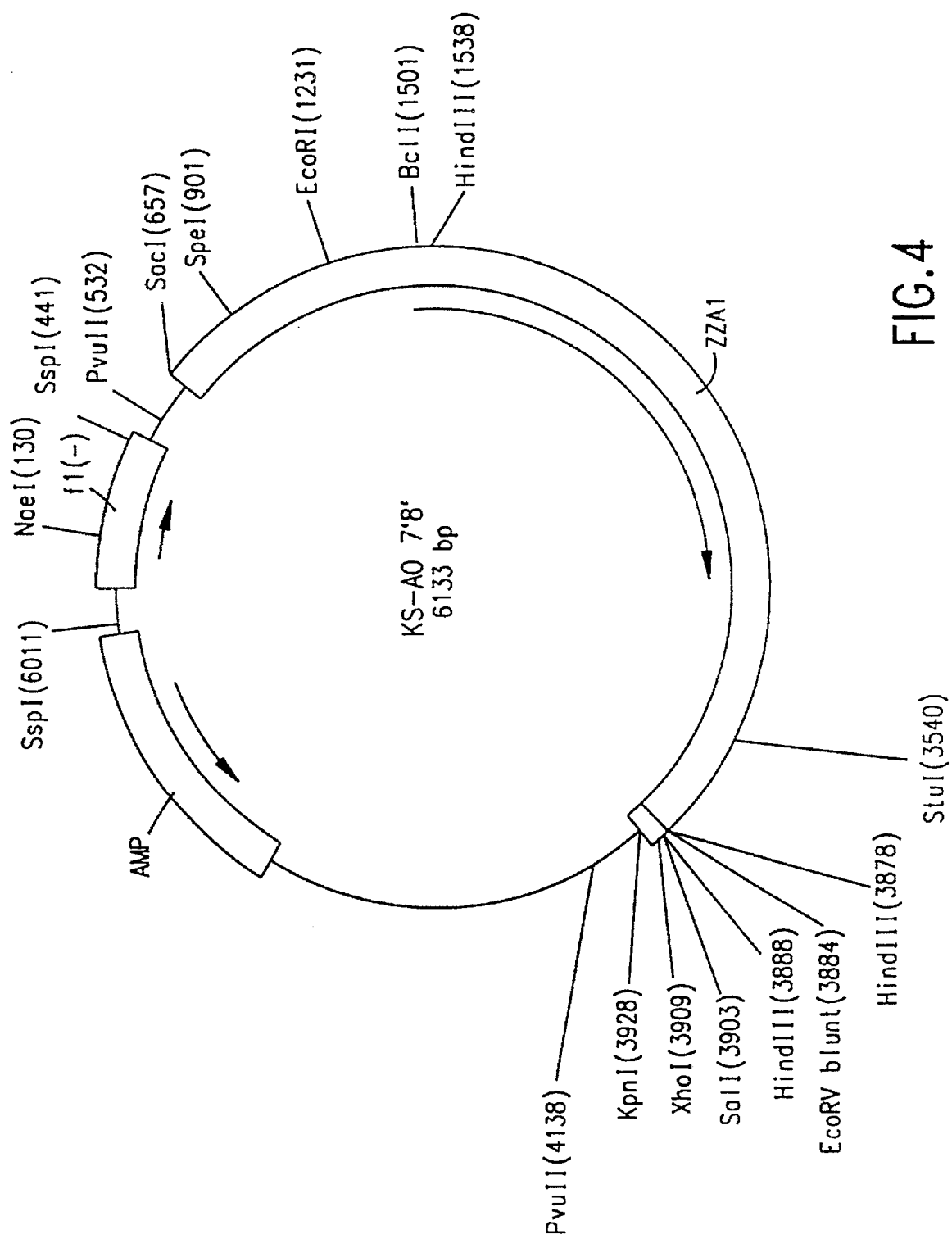
FIG. 4 is a map of the plasmid KS- A07'8'. This clone contains the 5' regulatory region of the ZZA1 gene, the protein ZZA1 structural gene, and the 3' noncoding region of the ZZA1 gene.
Figure 6:
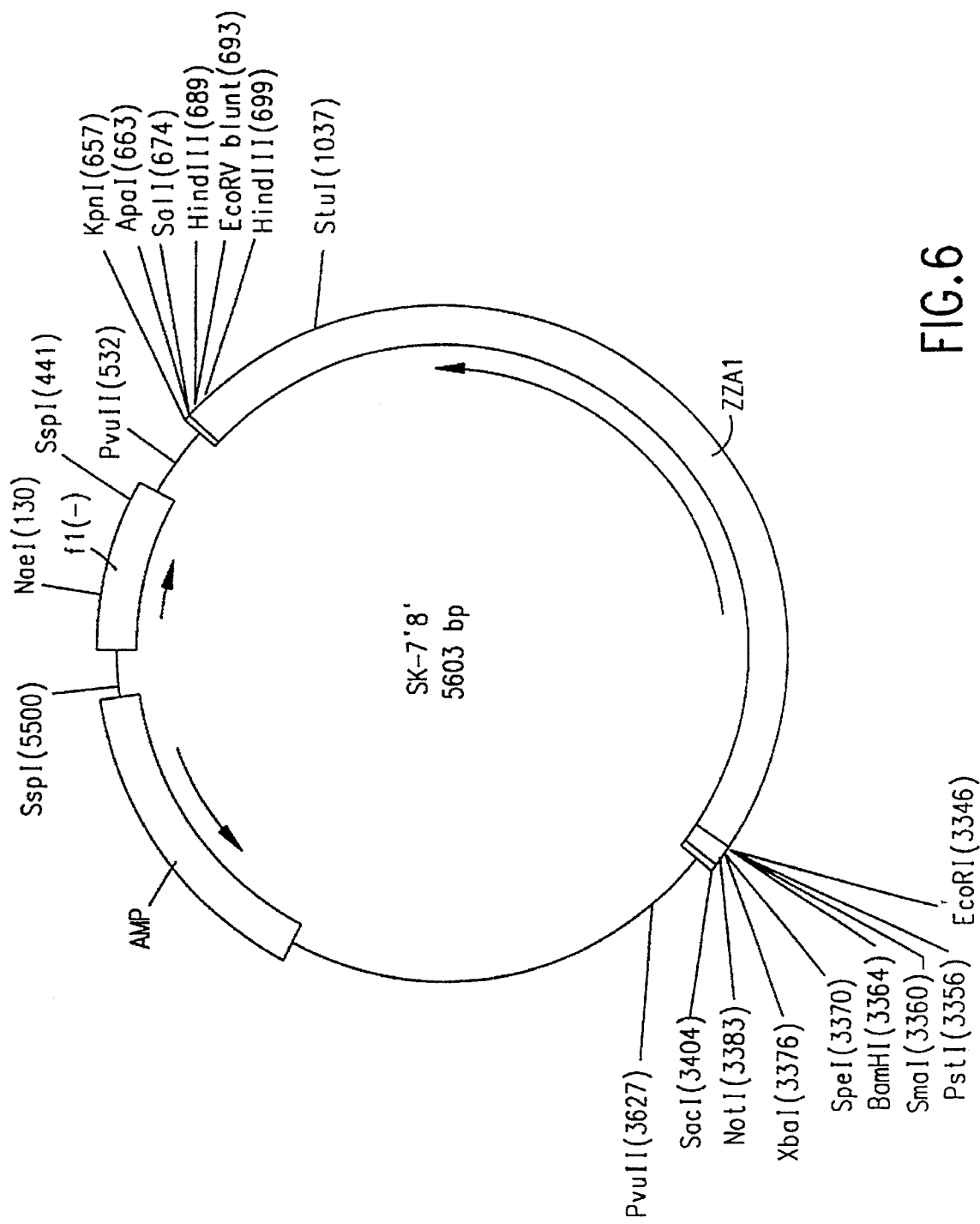
FIG. 6 is a map of the plasmid SK- 7'8'.

Three hundred nanograms of *Pichia Pastoris* genomic DNA digested with PstI and XhoI were amplified by PCR using a 25-mer oligonucleotide (5'TTGCACTCTGTTGGCTCATGACGAT 3') (SEQ ID NO:13) corresponding to the nucleotide sequence of AOX1 promoter and a 26-mer oligonucleotide (5'CAAGCTTGCACAAACGAACGTCTCAC 3') (SEQ ID NO:14) corresponding to a nucleotide sequence derived from the AOX1 terminator. The PCR conditions using *Thermus aquaticus* DNA polymerase (2.5 U; Perkin-Elmer Cetus) consisted of an initial 2 minute incubation at 97° C. followed by two cycles at 97° C. (1 min.), 45° C. (1 min.), 60° C. (1 min.), thirty-five cycles at 94° C. (1 min.), 45° C. (1 min.), 60° C. (1 min.), and a final DNA polymerase extension at 60° C. for 7 min. The 3273 bp fragment containing ZZA1 gene was phenol/chloroform treated and precipitated with ammonium acetate/ethanol. After digestion with SacI the fragment was purified by 1% low melt agarose electrophoresis and subcloned into the SacI/EcoRV sites in pBluescript KS–. A putative alcohol oxidase genomic clone KS– A07'8' (FIG. 4) was partially characterized by restriction mapping and dideoxy nucleotide sequencing. Comparison of 172 bp of ZZA1, AOX1, and AOX2 3' regions reveals that the ZZA1 and AOX1 terminators are 66% homologous to each other while ZZA1 and AOX2 terminators are only 24% homologous (FIG. 5). In order to obtain the entire nucleotide sequence of the ZZA1 gene an EcoRI/XhoI fragment was subcloned into pBluescript SK- (SKA07'8', FIG. 6).

Example 7

Figure 7:
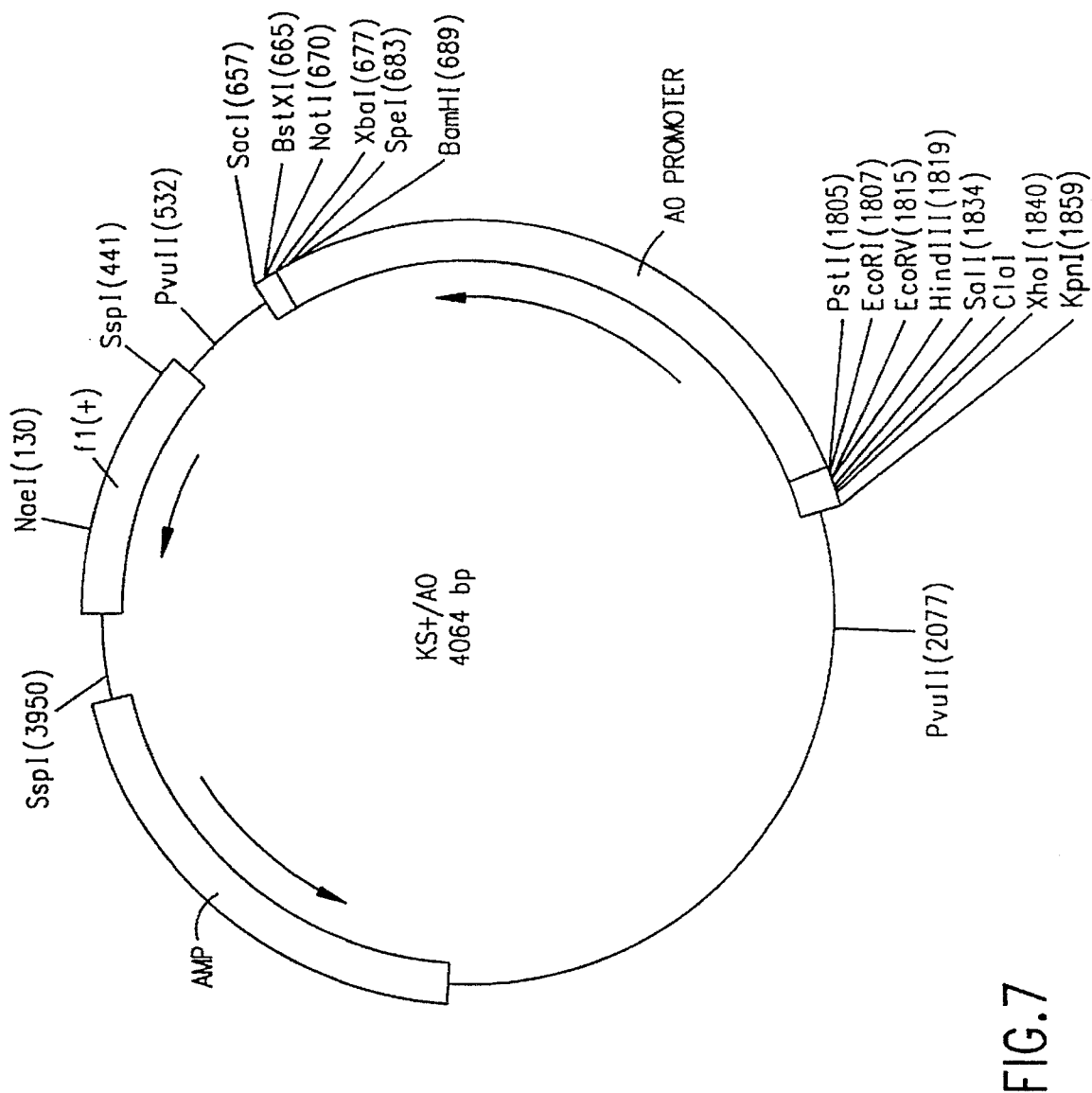
FIG. 7 is a map of the plasmid KS+/AO.
Figure 8:
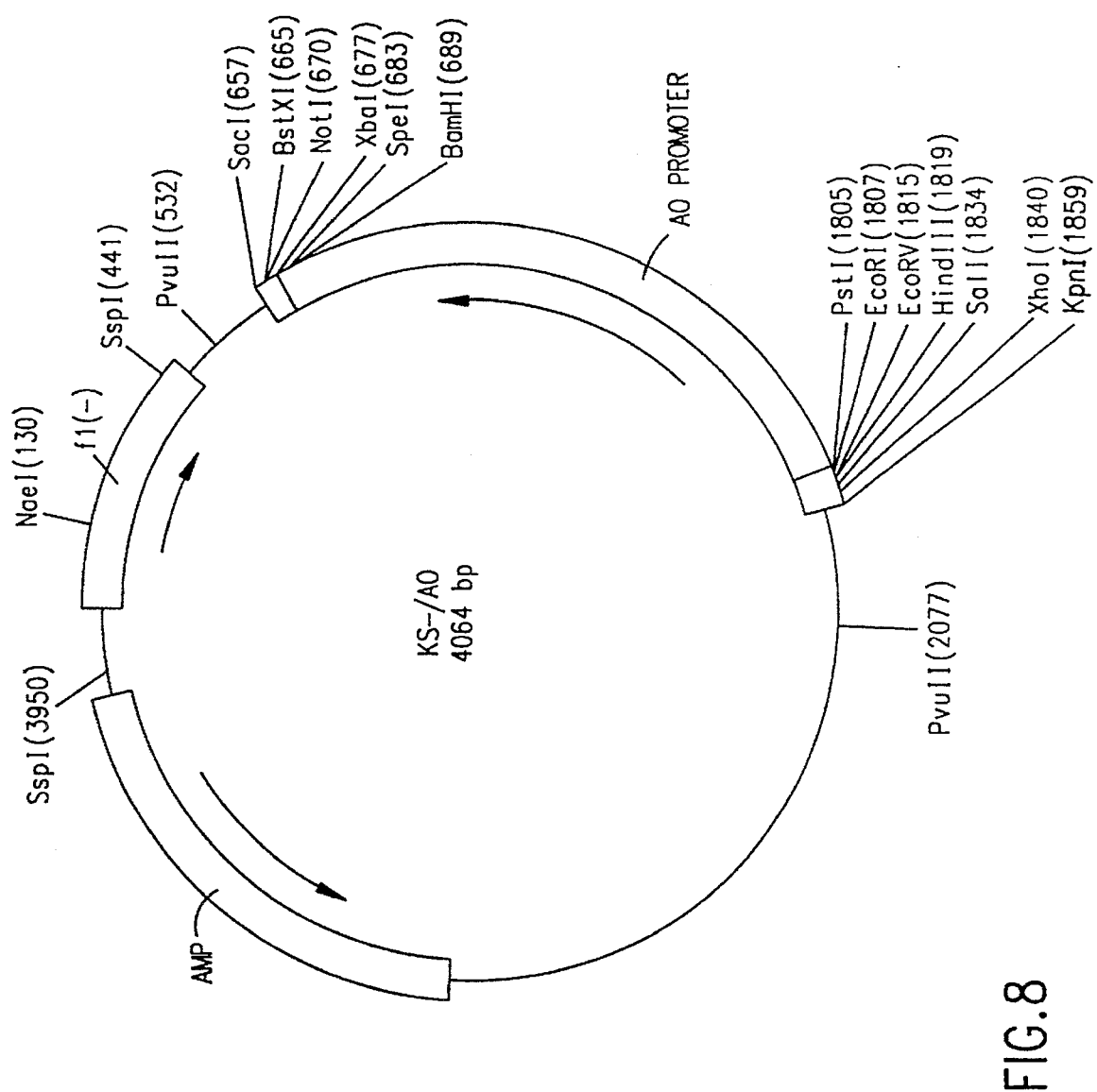
FIG. 8 is a map of the plasmid KS-/AO.

DNA sequencing A 1095 bp PstI, BamHI fragment containing the entire putative alcohol oxidase ZZA1 promoter was subcloned into pBluescript KS+and Bluescript KS- (Stratagene, La Jolla, Calif.). The nucleotide sequencing of KS+/AO (FIG. 7) and KS–/AO (FIG. 8) was carried out by dideoxy termination using single stranded templates. Nucleotide sequence analysis and amino acid sequence comparisons were performed using PCGENE™ and DNA Inspector™ IIE programs.

Example 8

Construction of ZZA1 regulatory region- rice α-amylase gene fusions

Figure 12:
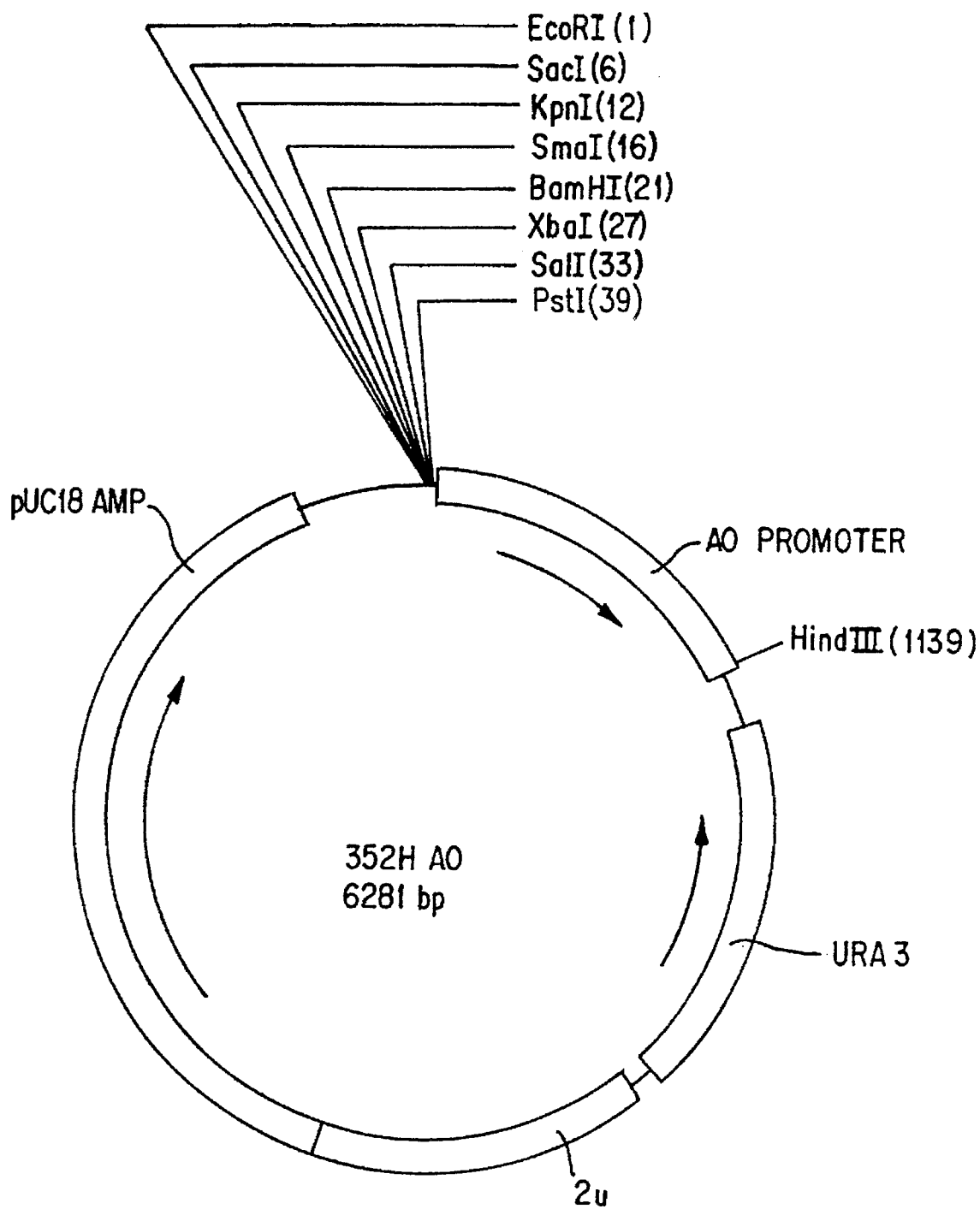
FIG. 12 is a map of the plasmid 352H AO.
Figure 13:
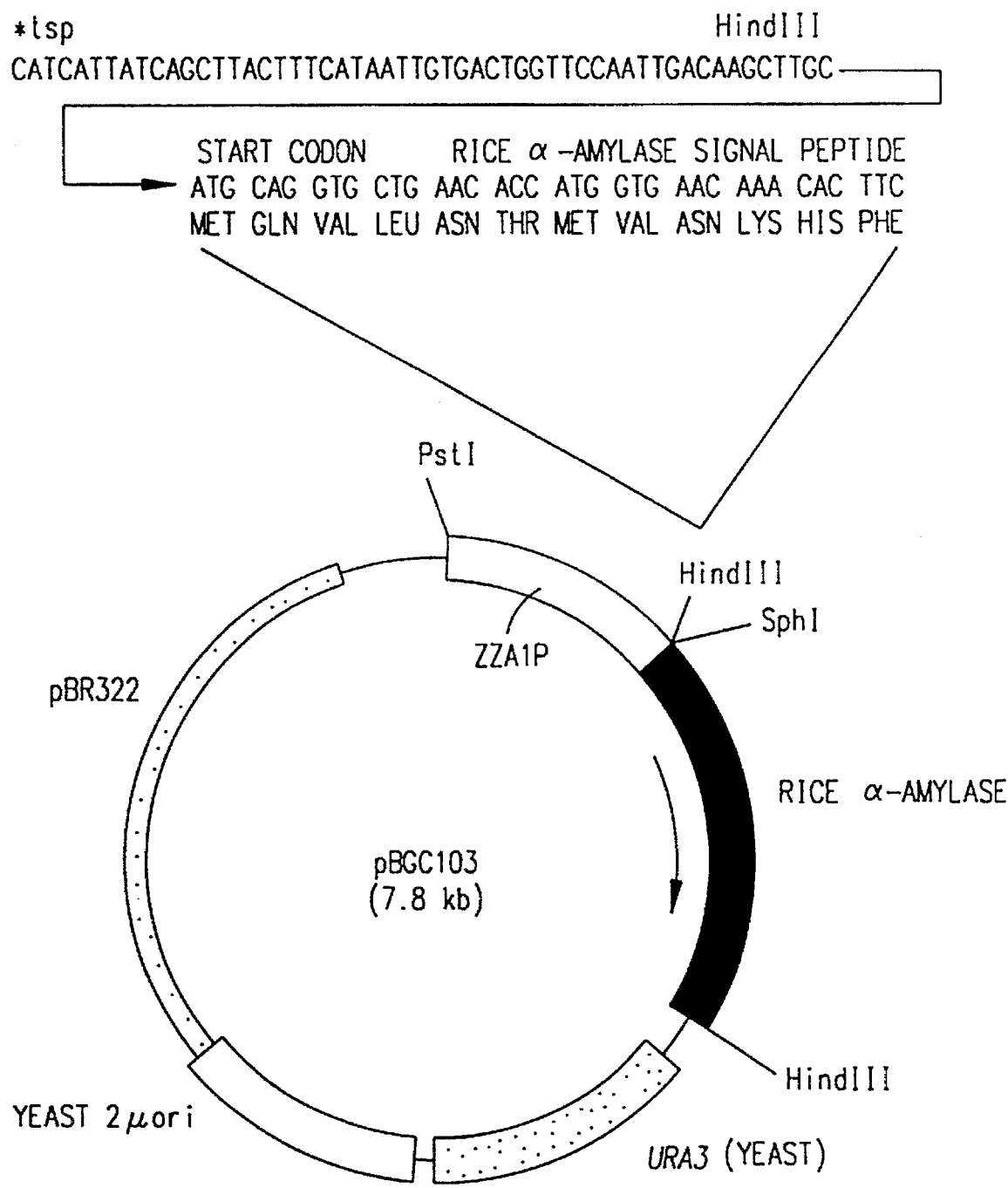
FIG. 13 is a map of the α-amylase expression vector, pBGC103. This plasmid contains the *Pichia pastoris* ZZA1 promoter, the rice α-amylase CDNA pOS103, *Saccharomyces cerevisiae* 2 μm ori, *Saccharomyces cerevisiae* URA3, and part of the pUC18 plasmid. The nucleotide explicitly recited in FIG. 13 is SEQ ID NO:15.

A 990 bp PstI, HindIII fragment containing the alcohol oxidase promoter was subcloned into YEp352 (American Type Culture Collection #37673). This resultant yeast expression vector 352H AO (FIG. 12) has a unique HindIII where foreign genes can be inserted. A 1.6 kb HindIII fragment from pUC18/103 was subcloned into the HindIII site of 352H AO. Plasmid pBGC103 (FIG. 13) contains the *Pichia pastoris* alcohol oxidase promoter, rice α-amylase cDNA pOS103 (GenBank #M24286), yeast 2 µm ori, yeast URA3, and part of pUC18 plasmid. The vector pBGC103 has the following nucleotide sequence (SEQ ID. NO:15) downstream of the putative transcription start point (tsp):

```
.tsp                                                              HindIII
5'CATCATTATCAGCTTACTTTCATAATTGTGACTGGTTCCAACCGACAAGC
3'GTAGTAATAGTCGAATGAAAGTATTAACACTGACCAAGGTTGGCTGTTCG NcoI
TTGC ATG CAG GTG CTG AAC ACC ATG GTG AAC AAA CAC TTC 3'
AACG TAC GTC CAC GAC TTG TGG TAC CAC TTG TTT GTG AAG 5'
(SEQ ID NO: 15)
```

Example 9

Starch-clearing plate assay for rice α-amylase expression

Yeast cells containing pBGC103 were grown on YEP, 1% starch, 5 mM CaCl$_2$ and incubated at 30° C. for three days. The plates were stained with iodine vapors and clear halos formed around yeast cells secreting active α-amylase. In order to directly select for amylolytic colonies the yeast cells containing pBGC103 were grown on DFM, pH 5.5, 1% starch, 5 mM CaCl$_2$ and incubated at 30° C. for three days. The plates were stained with iodine vapors and clear halos formed around yeast cells secreting active α-amylase.

Example 10

RNA Isolation and analysis 1403-ER40[pBGC103] was grown in YNBD and transferred to YEP, 0.5% methanol. Total RNA was isolated at 0, 2, 4, and 6 hr after methanol induction. The *Pichia pastoris* cells were grown in YEPD and transferred to YEP, 0.5% methanol. Total RNA was isolated from cells after 4 hr. The RNA was fractionated on a 1.1% glyoxal gel and transferred to nitrocellulose. The blot was probed with γ-$^{32}$P-dATP end-labeled 31-mer oligonucleotide (5'CGATGTATCCCCGAAG 3') (SEQ ID NO:16) complementary to the leader region of ZZA1. The transcription start point was determined using primer extension analysis of total RNA isolated from Pichia pastoris cells grown in YEP, 0.5% methanol. A 31-mer oligonucleotide (5'CGATGTATCCCCGAAG 3') (SEQ ID NO:16) complementary to the leader region of ZZA1 was end-labeled with $\gamma^{32}$-P DATP and T4 polynucleotide kinase and hybridized to RNA at 42° C. in a 10 µl reaction containing 400 mm KCl, 10 mM HEPES (pH 7.5), 1 mM EDTA for 12 hr. The reverse transcription reaction was initiated by the addition of 90 µl of 50 mM Tris pH 8.0, 10 mMMgCl$_2$, 0.4 mMDTT, 1 mM of each deoxynucleotide triphosphates, 1.25 units/ul of RNasin and 30 units of AMV reverse transciptase (Seikagaku). After a 42° C. incubation for 90 min the final EDTA concentration was changed to 20 mM. 10 µg of RNase was then added and the sample was incubated for 30 min at 37° C. The reaction mixture was brought to a final NH$_4$Ac concentration of 2M, extracted with phenol:chloroform:isoamyl alcohol (25:24:1), and precipitated with 2.5 volumes of ethanol. The cDNA was analyzed on an 8% polyacrylamide gel and the size of the extended product was determined by comparing it to a sequencing ladder of ZZA1 generated from the same end-labeled oligonucleotide primer.

Example 11

Figure 17:
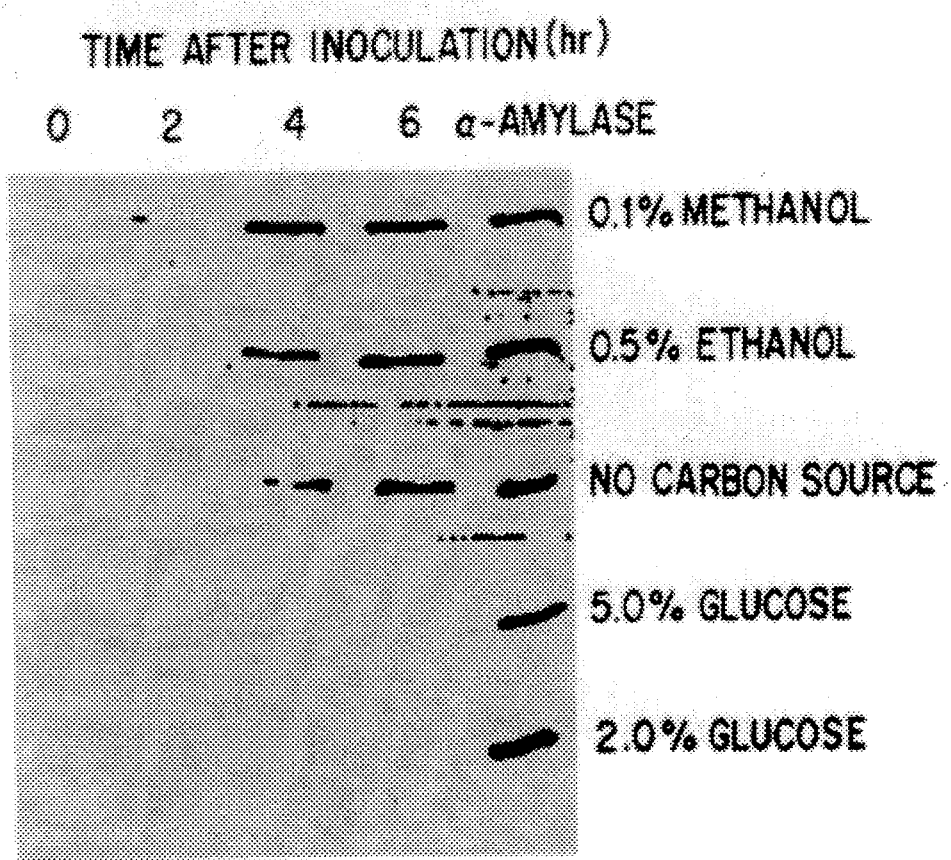
FIG. 17 is a western blot detecting the expression and secretion of α-amylase from yeast cells grown in 5 mM $CaCl_2$, YEP plus various carbon sources (methanol, ethanol, glucose, or no carbon source). Samples were removed from the culture 0, 2, 4, and 6, hours after inoculation.

Effects of carbon source utilization on α-amylase expression In order to quantify the expression of rice α-amylase, a 2.5 ml inoculum from strain 1403-ER40[pBGC103] grown in YNBD +trp (20 µg tryptophan per ml) was used to inoculate shake flasks containing 25 ml of YEP, 5 mM CaCl$_2$, 50 mM sodium acetate, pH 5.0, and various carbon souces. The cultures were incubated at 30° C. with agitation (300 rpm). Samples were removed from the cultures after 44 hours and briefly centrifuged. A microassay was used to measure enzyme kinetics. The reaction was initiated by adding 50 µl of supernatant to 1000 µl of substrate (Sigma Kit #576-3). One unit of (α-amylase activity is defined as the amount of enzyme required to liberate 1 mmol of NADH/min. Each sample was assayed for enzyme activity at 25° C. Total soluble protein concentrations were determined using BSA as a standard. 12 µl of supernatant from each sample was analyzed on a 0.1% SDS, 12.5% polyacrylamide gel and transfered by electroblotting for 1 hour to a nitrocellulose membrane. The blotted membrane was incubated for 1 hour with a 2000-fold dilution of rabbit anti-α-amylase antiserum. The enhanced chemiluminescence horseradish peroxidase-linked, goat anti-rabbit IgG (Cappel) was developed according to the manufacturer's (Amersham) specifications. The autoradiogram was exposed for <30 seconds. The quantity of secreted α-amylase was estimated by comparing the crude extract autoradiogram signal to the signal obtained from known quantities of purified α-amylase. In order to study the effects of various carbon sources on the expression of rice α-amylase, an inoculum from strain 1403-ER40[pBGC103] grown in YNBD+trp (20 µg tryptophan per ml) was used to inoculate shake flasks containing YEP, 5 mM CaCl$_2$, and various carbon sources at a final optical density of A$_{600}$=0.5/ml. The cultures were incubated at 30° C. with agitation (300 rpm) and samples were removed from the cultures at 0, 2, 4, and 6 hr after inoculation. Equal volumes from each sample was subjected to Western analysis on a 12.5% PAGE as previously described with the following modifications. The blotted membrane was incubated for 1 hour with a 3000-fold dilution of rabbit anti-α-amylase antiserum and the autoradiogram was exposed for 5 minutes. Results of the experiment can be seen in FIG. 17.

Example 12

Purification of alcohol oxidase

Pichia pastoris cells grown in YEP, 0.5% methanol were frozen in liquid nitrogen, and vortexed with glass beads in 20 mM Tris-HCL, pH 8.0. The suspension was centrifuged and the supernatant was bound on a FPLC Mono Q ion-exchange column (Pharmacia). The sample was eluted with a linear NaCl gradient (0–1M NaCl in 20 mMTris-HCL, pH 8.0), and the fractions were assayed for alcohol oxidase activity. The N-terminal sequence of the purified protein was obtained using an automated protein sequenator. The N-terminal sequence NH$_3$-Ala-Ile-Pro-Glu-Glu-Phe-Asp-Ile-Ile-Val-Cys-Gly -Gly-Gly-Ser-COOH (SEQ ID NO:17) obtained from the purified protein was identical to the amino acid sequence deduced from the ZZA1 genomic clone.

Example 13

Regulation of α-amylase production in Saccharomyces cerevisiae

In order to study the effects of various carbon sources on the expression of rice a-amylase, a 2.5 ml inoculum from strain 1403-ER40[pBGC103] grown in YNBD +trp (20 µg tryptophan per ml) was used to inoculate shake flasks containing 25 ml of YEP, 5 mM CaCl$_2$, 50 mM sodium acetate, pH 5.0 and various carbon sources. The cultures were incubated at 30° C. with agitation (300 rpm). Samples were removed from the cultures after 44 hours and briefly centrifuged. A microassay was used to measure enzyme kinetics. The reaction was initiated by adding 50 µl of supernatant to 1000 µl of substrate (Sigma® Kit #576-3). One unit of α-amylase activity is defined as the amount of enzyme required to liberate 1 mmol of NADH/min. Each sample was assayed for enzyme activity at 250° C. The results are summarized in the Table I.

TABLE I

Rice α-amylase activity in Saccharomyces cerevisiae transformants

| Strain (U/L) | Carbon Source | | α-amylase activity |
|---|---|---|---|
| 1403-ER40 | 5% | glucose | 0 |
| 1403-ER40[pBGC103] | 0 | | 7.1 |
| 1403-ER40[pBGC103] | 2% | glucose | 49.4 |
| 1403-ER40[pBGC103] | 5% | glucose | 2.4 |
| 1403-ER40[pBGC103] | 2% | sucrose | 101.2 |
| 1403-ER40[pBGC103] | 5% | sucrose | 82.4 |
| 1403-ER40[pBGC103] | 34 | glycerol | 72.9 |
| 1403-ER40[pBGC103] | 24 | ETOH | 58.8 |
| 1403-ER40[pBGC103] | 5% | ETOH | 25.9 |

Total soluble protein concentrations were determined using BSA as a standard. 12 µl of supernatant from each sample was analyzed on a 0.1% SDS, 12.5% polyacrylamide gel and transferred by electroblotting for 1 hour to a nitrocellulose membrane. The blotted membrane was incubated for 1 hour with a 2000-fold dilution of rabbit anti-α-amylase antiserum. The enhanced chemiluminescence horseradish peroxidase-linked, goat anti-rabbit IgG (Cappel) was developed according to the manufacturer's (Amersham) specifications. The autoradiogram was exposed for <30 seconds. The quantity of secreted α-amylase was estimated by comparing the crude extract autoradiogram signal to the signal obtained from known quantities of purified α-amylase. Western blot analysis of secreted proteins was performed on 1403-ER40[pBGC103] grown in various carbon sources. A Western blot was performed in which the following lanes were run. (Lane 1: 0.15 μg of purified rice α-amylase; 2: 0.75 μg of purified α-amylase; 3: Cells containing pBGC103 were grown in YEP, 5 mM CaCl$_2$, 50 mMNaAcetate, pH 5.0 and 3% glycerol; 4: 2% ethanol; 5: 2% glucose; 6: 2% sucrose; 7: 3% starch (ammonium sulfate precipitated extra-cellular proteins); 8: 3% starch (phenyl superose FPLC purified protein)). The Western blot results indicated that the α-amylase produced by ER40[pBGC103] was secreted in excess of 25 μg/ml. Alpha amylase was produced in the presence of ethanol.

Example 14

Figure 14:
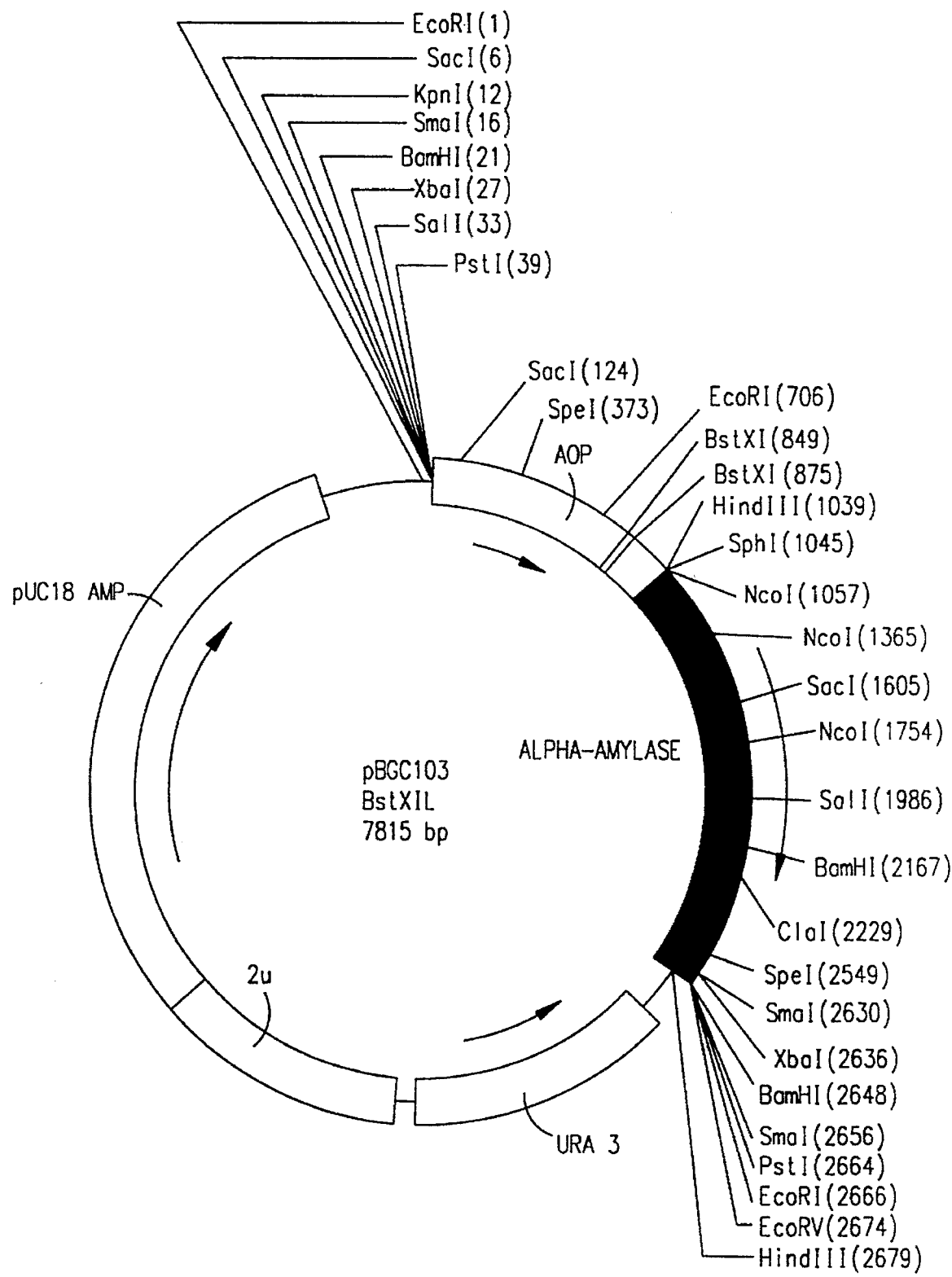
FIG. 14 is a map of the plasmid pBGC103 BstXII.

Construction of ZZA1 BstXI site directed mutant regulatory region- rice α-amylase gene fusions A rice α-amylase expression vector, pBGC103 BstXIL, containing an additional TTCCAA core consensus sequence in the ZZA1 promoter was constructed. A 30 bp BstXI fragment, made by annealing a 30-mer oligonucleotide (5'CTGGTCTAGACATTGTATGCTTCCAAGTTT 3') (SEQ ID NO:18) to a 30-mer oligonucleotide (5'TTGGAAGCATACAATGTCTAGACCAGAAAC 3') (SEQ ID NO:19), was subcloned into the BstXI site of pBGC103. The resultant new plasmid, pBGC103 BstXIL (FIG. 14), contains a mutant *Pichia Pastoris* alcohol oxidase promoter containing an additional TTCCAA core consensus sequence, rice α-amylase cDNA pOS103 (GenBank #M24286), yeast 2 μm ori, yeast URA3, and part of pUC18 plasmid. The *Pichia -pastoris* alcohol oxidase ZZA1 promoter has the following nucleotide sequence:

was transformed with pBGC103. Cultures of ER40 [pBGC103] grown in YEP 3% starch were analyzed for rice α-amylase activity and ETOH production (Sigma kits #576-3, #332). Yeast DNA was isolated, analyzed by PCR, and transformed into *E. coli* CGOO. Restriction digests of miniscreen DNA isolated from the transformants indicate that pBGC103 was maintained in an extrachromosomal state and had not undergone any detectable intramolecular rearrangements.

Example 16

Comparison of α-amylase production in Saccharomyces cerevisiae ER40rpBGC103]to ER401uBGC103 BstXILI In order to compare the relative expression of rice α-amylase from *Saccharomyces cerevisiae* ER40 [pBGC103]to ER40[pBGC103 BstXILI , 2.5 ml inoculum from strain ER40[pBGC103]and strain ER40[pBGC103 BstXILI grown in YNBD+trp (20 μg tryptophan per ml) were used to inoculate shake flasks containing 50 ml of YEPD. The cultures were incubated at 30° C. with agitation (300 rpm). Samples were removed from the cultures after 48 hours and briefly centrifuged. A microassay was used to measure enzyme kinetics. The reaction was initiated by adding 50 μl of supernatant to 1000 μl of substrate (Sigma Kit #576-3). One unit of α-amylase activity is defined as the amount of enzyme required to liberate 1 mmol of NADH/min. Each sample was assayed for enzyme activity at 25° C. The results are summarized in the Table II.

```
NsiI                            BstXI
5' ATGCATTGTTCTCCACATTGTATGCTTCCAAGTTTCTGG 3'
3' TACGTAACAAGAGGTGTAACATACTAAGGTTCAAAGACC 5'
(SEQ ID NO: 20)
```

Two oligonucleotides used in the site directed mutagenesis of the ZZA1 promoter have the following nucleotide sequence:

```
BstX1 XbaI              BstXI
   5'CTGGTCTAGACATTGTATGCTTCCAAGTTT 3' (SEQ ID NO: 21)
3'CAAAGACCAGATCTGTAACATACGAAGGTT 5'     (SEQ ID NO: 22)
```

The vector pBGC103 BstXIL containing the *Pichia pastoris* alcohol oxidase promoter and rice α-amylase cDNA pOS103 has the following nucleotide sequence:

```
    NsiI                            BstXI              XbaI
5'ATGCATTGTTCTCCACATTGTATGCTTCCAAGTTTCTGGTCTAGA
3'TACGTAACAAGAGGTGTAACATACTAAGGTTCAAAGACCAGATCT

BstXI
CATTGTATGCTTCCAAGTTTCTGG 3'
GTAACATACGAAGGTTCAAAGACC 5'
(SEQ ID NO: 23)
```

Example 15

Transformation and analysis of 1403-ER40[pBGC103]

1403-ER40, an ethanol tolerant strain of *S. cerevisiae* (MATα, qa13, qa14, mel, SUC+, MAL4, MGL3, trpl, ura3),

TABLE II

Rice α-amylase activity in *Saccharomyces cerevisiae* transformants

| Strain (U/L) | Carbon Source | α-amylase activity |
|---|---|---|
| 1403-ER40[pBGC103] | 2% glucose | 35.3 |
| 1403-ER40[pBGC103 BstXILI | 2% glucose | 96.5 |

28 µl of supernatant from each sample was analyzed on a 0.1% SDS, 12.5% polyacrylamide gel and transferred by electroblotting for 1 hour to a nitrocellulose membrane. The blotted membrane was incubated for 1 hour with a 2000-fold dilution of rabbit anti-α-amylase antiserum. The enhanced chemiluminescence horseradish peroxidase-linked, goat anti-rabbit IgG (Cappel) was developed according to the manufacturer's (Amersham) specifications. The autoradiogram was exposed for <30 seconds. The results of the Western blot analysis of secreted proteins from 1403-ER40 [pBGC103] and 1403-ER40[pBGC103 BstXILI are in FIG. 17.

Example 17

Purification of α-amylase from *S. cerevisiae*

A 50 ml inoculum from strain ER40[pBGC103] grown in YNB+trp (0.67% yeast nitrogen base without aa, 0.2% glucose, 20 µg tryptophan per ml) was used to inoculate.

500 ml of YEP, 3% potato starch, 5 mM CaCl$_2$ (pH 5.0). The culture was grown in a shake flask for 40 hrs at 30° C. with agitation (300 rpm). After spinning down the cells the supernatant was concentrated by ammonium sulfate precipitation (60%). The pellet was resuspended in approximately 10 mls of 10 mM Tris pH 7.4, 1M ammonium sulfate. The crude enzyme was then purified using phenyl superose HR 10/10 column chromatography (Pharmacia FPLC, 1–0M ammonium sulfate gradient). The α-amylase was eluted in fraction 66 and its enzyme activity was analyzed (Sigma Kit 576-3).

Example 18

Gel mobility shift assays

A *Pichia pastoris* nuclear extract is prepared by growing the yeast cells in 250 mls of YNB (minimal) media plus 0.5% methanol (induction media) or 5% glucose (repression media) for 48 hours at 30° C. The cells are pelleted by centrifugation at 3,000 rpm for 5 minutes. The pellets are washed once in ddH20, once in SED, once in im sorbitol, and then they are resuspended in 25 ml of 0.1M tris-HCL, pH 7.0, and 1M sorbitol. The cells are mixed with 750 µl Zymolyase 100,000 (Seikagaku) and are incubated at 30° C. for 1 hour. The resulting spheroplasts are centrifuged at 1,000 g for 5 minutes and resuspended in a glass bead disruption buffer containing 50 MM Tris-HCL, pH 7.9, 5 mMMgCl$_2$, 1 nM dithiothreitol, 0.2 mM EDTA, 2.5 mM phenylmethylsulfonyl fluoride, 10% dimethyl sulfoxide, and 20% glycerol. The whole-cell extracts are quickly frozen by dropwise addition into liquid nitrogen. In some preparations 2 µM pepstatin A and 0.6 µM leupeptin are included.

DNA-binding assays are performed in 5 µl reaction mixes containing 15 mM Tris-HCL (pH 7.4), 50 mM KCL, 1 mM EDTA, 0.5 mM dithiothreitol, 50 µg of bovine serum albumin per ml, 0.05% Nonidet P-40, 25 µg of poly (dI-dC) per ml, 6% glycerol, 2 fmol of 5'-end-labeled DNA probe (specific activity, 5×10$^6$ dpm/pmol), and 1 to 20 µg of whole-cell extract protein. The reactions are incubated for 2 to 20 minutes at 21° C., then 15 µl of 10 mM Tris-HCL (pH 7.4), i mM EDTA, 0.05% bromophenol blue, 0.05% xylene cyanol blue, and 6% glycerol is added. The binding reactions are subjected to electrophoresis for 2 hours at 4 V/cm at 4° C. on a 1.5% agarose gel in buffer containing 50 mM Tris-borate (pH 8.3) and 1 mM EDTA. After electrophoresis the gel is dried on Whatman DE81 chromatography paper and subjected to autoradiography, Competition DNA-binding assays are performed as described above in the absence of poly(dI-dC). Unlabeled competitor DNA is added to the binding reaction mixture. The oligonucleotide probes used in this experiment have the following nucleotide sequences:

| | | | |
|---|---|---|---|
| 5' | TTGTATGCTTCCAAGTTTCTGGT | 3' | (SEQ ID NO: 24) |
| 5' | ACACCCGCTTTTTGG | 3' | (SEQ ID NO: 25) |

Example 19

Isolation of methanol induced trans-acting factor

A random primed cDNA library is constructed using poly(A) RNA prepared from *Pichia pastoris* cells grown in 250 mls of YNB (minimal) media plus 0.5% methanol (induction media). The amplified library is screened with a labeled oligonucleotide fragment that consists of the TTC-CAA motif.

Example 20

Isolation of methanol specific transacting factor by using an alcohol oxidase promoter shuttle vector A PstI-KpnI fragment containing the ZZA1 promoter and the rice α-amylase cDNA OS103 is subcloned into YIp5. This vector is then integrated into 334 by Leu2+ complementation.

A random primed cDNA library is constructed in 352H AO using poly(A) RNA prepared from *Pichia Pastoris* cells grown in 250 mls of YNB (minimal) media plus 0.5% methanol (induction media). The amplified cDNA library is transformed into 334[YIp5 AO 103] and recombinant yeast cells are selected on DFM plus 1% starch. Putative clones coding for methanol trans-acting factors are identified by the production of large halos.

Example 21

Transformation and analysis of strain 1403-ER40 [pBGC103]

1403-ER40, an ethanol tolerant strain of *S. cerevisiae* (MATs, gal3, gal4, mel, SUC+, MAL4, MGL3, trpl, ura3), was transformed with pBGC103. Cultures of ER40 [pBGC103]grown in YEP 3% starch were analyzed for rice α-amylase activity and ETOH production (Sigma® kits, catalogue numbers 576-3 and 332, respectively). Yeast DNA was isolated, analyzed by PCR, and transformed into *E. coli* C600. Restriction digests of miniscreen DNA isolated from the transformants indicate that pBGC103 was maintained in an extrachromosomal state and had not undergone any detectable intramolecular rearrangements.

Example 22

Construction of ZZA1 regulatory region- rice α-amylase gene fusions for expression in *Hansenula polymorpha*

Figure 16:
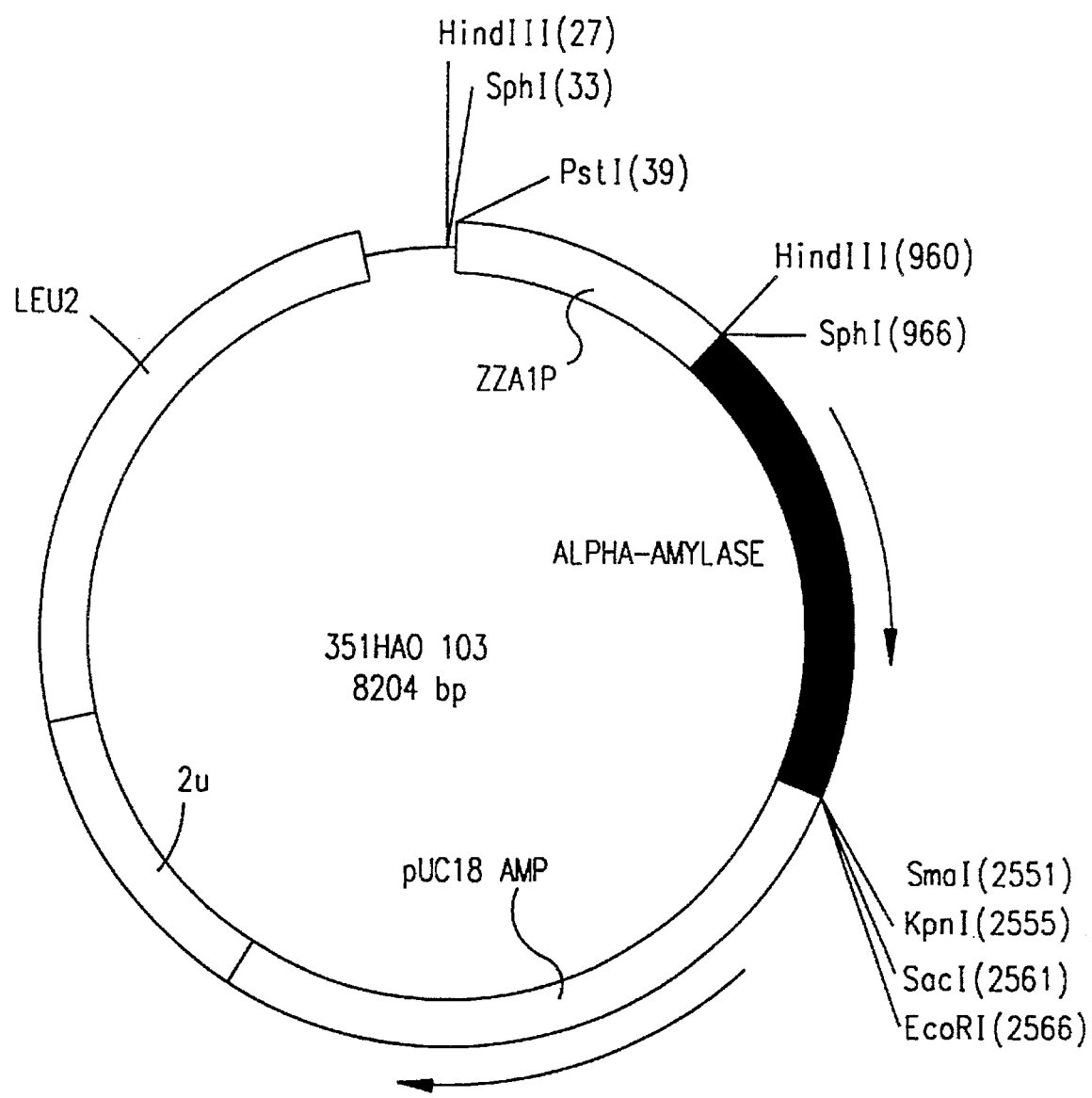
FIG. 16 is a map of the plasmid 351 HAO103.

A 2512 bp PstI, SmaI fragment containing the alcohol oxidase promoter and the rice α-amylase cDNA OS103 was subcloned into YEp351. This yeast expression vector is called 351HAO 103 (FIG. 16) and contains the *Pichia-pastoris* alcohol oxidase promoter, rice α-amylase cDNA pOS103 (GenBank #M24286), yeast 2 μm ori, yeast LEU2, and part of the pUC18 plasmid. The vector 351HAO 103 has the following nucleotide sequence downstream of the putative transcription start point (tsp):

```
.tsp                                                          HindIII
5'CATCATTATCAGCTTACTTTCATAATTGTGACTGGTTCCAACCGACAAGC
3'GTAGTAATAGTCGAATGAAAGTATTAACACTGACCAAGGTTGGCTGTTCG
                    NCOI
TTGC ATG CAG GTG CTG AAC ACC ATG GTG AAC AAA CAC TTC 3'
AACG TAC GTC CAC GAC TTG TGG TAC CAC TTG TTT GTG AAG 5'
(SEQ ID NO: 15)
```

Example 23

Transformation and analysis of *Hansenula polymorpha* [351HAO 103]

A 24 hour 50 ml culture of the methylotrophic yeast, *Hansenula polymorphs* (leu1-1), was grown in YEPD at 30° C. The cells were pelleted, washed once with LITE (0.1M Lithium acetate, 10 mM Tris pH 7.6, 1 mM EDTA), resuspended in 1 ml LITE, and incubated at 30° C. for 1 hour with agitation. The competent *Hansenula polymorphs* cells were transformed with 351HAO 103. Cultures of *Hansenula polymorpha* [351 HAO 103]#18 grown in YEP 0.5 & methanol, 5 mM CaCl₂ were analyzed for rice α-amylase activity (Sigma® kits #576-3).

Example 24

Construction of ZZA1 alcohol oxidase expression vector

A 2512 bp HindIII fragment containing the alcohol oxidase ORF was subcloned into 352H AO. This yeast expression is called pBGC104 and contains the *Pichia pastoris* alcohol oxidase gene ZZA1, yeast 2 μm ori, yeast URA3, and part of the plasmid pUC18.

Example 25

Figure 3:
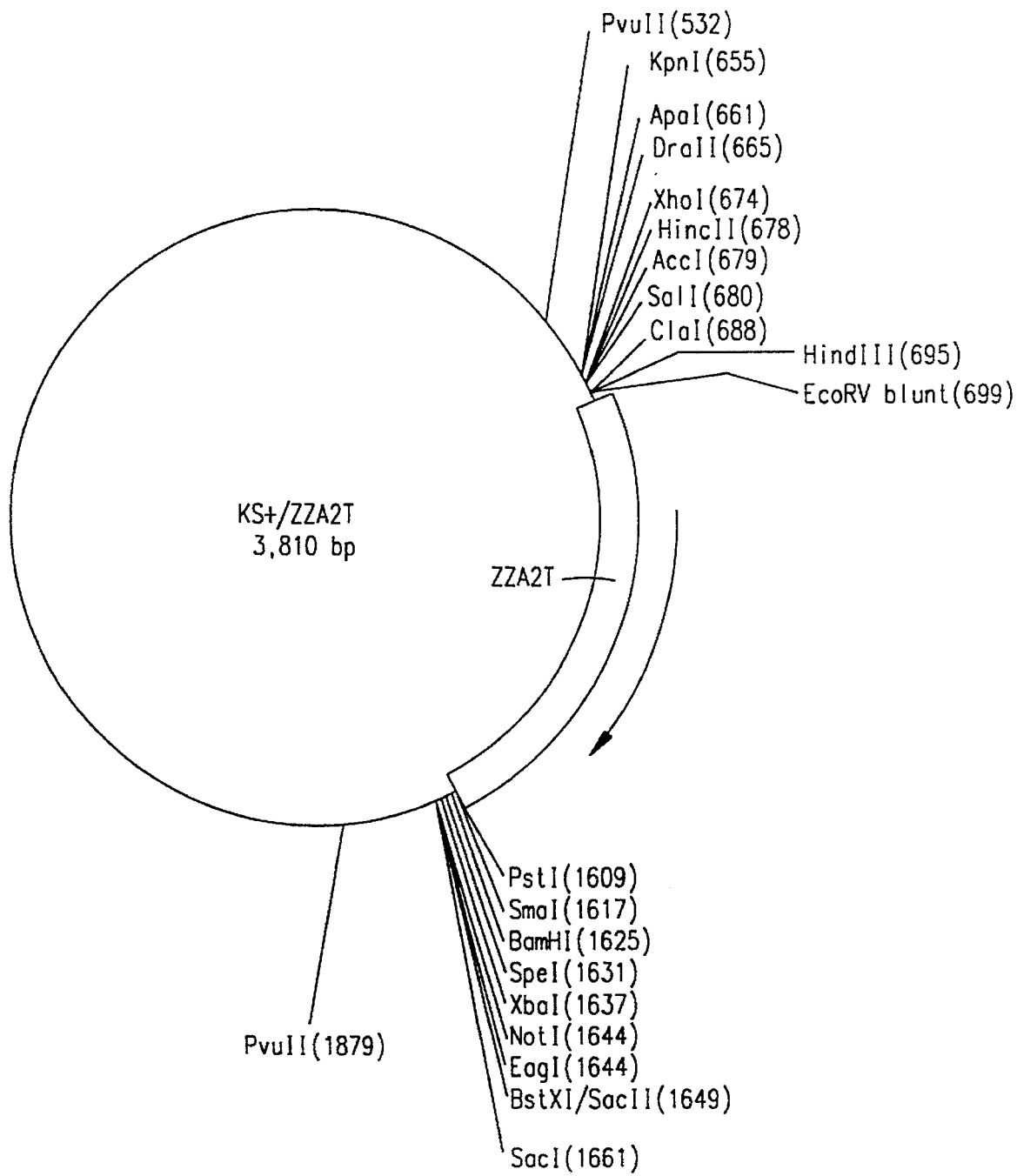
FIG. 3 is a map of the plasmid KS+ZZA2T.

Isolation of Alcohol Oxidase ZZA2 terminator 1.5 micrograms of Pichia pastoris genomic DNA digested with PstI and XhoI was amplified by PCR using a 24 -mer oligonucleotide (5'TCG ACC CAG GTT TCA TGA ACG ATG 3')(SEQ ID NO:4) corresponding to the nucleotide sequence of AOX1 and AOX2 ORF and a 31-mer oligonucleotide (5'TCC TGC AGC AAC CAA TGA GGA GAA TGA CAA C 3') (SEQ ID NO:5) corresponding to a nucleotide sequence derived from the AOX2 terminator. The PCR conditions using *Thermos aquaticus* DNA polymerase (2.5 U; Perkin-Elmer Cetus) consisted of an initial 2 minute incubation at 97° C followed by five cycles at 97° C. (1 min.), 45° C. (1 min.), 60° C (2.5 min.), thirty-five cycles at 94° C. (1 min.), 45° C. (0.5 min.), 60° C. (2.5 min.), and a final DNA polymerase extension at 60° C. for 7 min. The 910 bp fragment containing ZZA02 gene was phenol/chloroform treated and was precipitated with ammonium acetate/ethanol. After digestion with PstI the fragment was purified by 1% low melt agarose electrophoresis and subcloned into the EcoIV/PstI sites in pBluescript KS+. The resultant plasmid, KS+ZZA2T (FIG. 3 ), is a putative alcohol oxidase genomic clone containing a terminator sequence.

Biological Deposits

On Sep. 15, 1992, Applicants have deposited with the American Type Culture Collection, Rockville, Md., USA (ATCC) the plasmid pBGC103, in *S. cerevisiae*, described herein, under ATCC accession no. 74185. On Jan. 6, 1993, Applicants have deposited with the American Type Culture Collection, Rockville, Md., USA (ATCC) the plasmid pBGC104, in *E. coli*, described herein, under ATCC accession no. 69181. On Mar. 11, 1994, Applicants have deposited with the American Type Culture Collection, Rockville, Md., USA (ATCC) the plasmid KS+/ZZA2T, in *E. coli* JM109, described herein, under ATCC accession no. 69585. These deposits were made under the provisions of the Budapest Treaty on the International Recognition of the Deposit of Microorganisms for the purposes of patent procedure and the Regulations thereunder (Budapest Treaty). This assures maintenance of a viable culture for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

Equivalents

All publications and patents mentioned in the above specification are herein incorporated by reference. The foregoing written specification is considered to be sufficient to enable one skilled in the art to practice the invention. Indeed, various modifications of the above-described modes for carrying out the invention which are obvious to those skilled in the field of molecular biology or related fields are intended to be within the scope of the following claims.

SEQUENCE LISTING ( 1 ) GENERAL INFORMATION:

( i i i ) NUMBER OF SEQUENCES: 57

( 2 ) INFORMATION FOR SEQ ID NO:1:

( i ) SEQUENCE CHARACTERISTICS:
( A ) LENGTH: 1095 base pairs
( B ) TYPE: nucleic acid
( C ) STRANDEDNESS: unknown
( D ) TOPOLOGY: unknown ( i i ) MOLECULE TYPE: DNA ( x i ) SEQUENCE DESCRIPTION: SEQ ID NO:1:

| | | | | | | |
|---|---|---|---|---|---|---|
| CTGCAGCTTT | GATACCTGAA | ATTCCTGAGC | CTATAATAAT | GACTTTTGCA | CTCTGTTGGC | 60 |
| TCATGACGAT | TTTGTTGAAA | TGAATCTTCA | CAAGAAGAGC | TCAATTGAGT | AGAGATAATT | 120 |
| AGTAAGTGAG | ATCCAACACC | CAGGAACGAG | ATGGATTCAG | GAGAAATTGT | TCTGCCATCC | 180 |
| GACATCGACA | AGTTAGACAC | AATAGTGCCA | AATGCAGAGG | GGACGTTTCC | TCAAGGCAAG | 240 |
| AACTCCACTT | TATTCCTCCT | CAAACACCCG | CCTTCGCCGT | TAAAAACCAG | CCCAGTTACT | 300 |
| AAACATGGTT | TGGACTCTCT | CTAATCCACT | TTGTTAGGCT | ACTAGTAGCA | TTATTTTCTT | 360 |
| AGCCTGTCTA | TATGGTTCCT | TGCGAGTTTT | TAATTTTATT | TCTATTTCCG | AATGTAACTT | 420 |
| ACTCCGCATT | CCATCCCAAC | ACCAGAAAGT | TGAGGGTTTT | TGTGAGTGTG | GGGTCGGTAA | 480 |
| CAGTTTCATG | TTCCCCCAAT | GGCCTAAAAT | TGACACTTTA | GACGCCCTGT | TCAAACTCAA | 540 |
| ATTGACAAAA | GCGTGATCTC | ATCAGAGATG | AACTAGGTTT | GGTTCGATCA | AAAGCTAACG | 600 |
| GCCAGTTGGT | CAAAAGAAA | CTTCCAATGT | CGGCATACCG | TTTGTTTCGT | TTGACCCGAC | 660 |
| AATTGATGTT | GAAGAATTCC | CTCTTACACT | TAGCGCAGCC | TTTATTTTGC | TTGGGGTCTC | 720 |
| GCTGCGCTTG | GGTCTCGGTG | TGCTTGTGAC | CGGAAACGCA | AATGGGGAAA | CACCCGCTTT | 780 |
| TTGGATGATT | ATGCATTGTT | CTCCACATTG | TATGCTTCCA | AGTTTCTGGT | GGGAATACTG | 840 |
| ATAGCCTAAC | GTTCATGATC | AAAACTAATG | TCTTCCCTAC | TTGAACAGCA | ATATATAAAC | 900 |
| AGAAGAAGAT | TTCCTTTCTA | AGGTCTTTTT | TTTTATCATC | ATTATCAGCT | TACTTTCATA | 960 |
| ATTGTGACTG | GTTCCAATTG | ACAAGCTTTT | GATTCTAACG | ACTTAACGA | CAACCTAAAG | 1020 |
| AACAAAAACA | ACTAATTATT | CGAAACAATG | GCTATTCCCG | AAGAATTTGA | TATTATCGTC | 1080 |
| TGTGGTGGTG | GATCC | | | | | 1095 |

( 2 ) INFORMATION FOR SEQ ID NO:2:

( i ) SEQUENCE CHARACTERISTICS:
( A ) LENGTH: 23 base pairs
( B ) TYPE: nucleic acid
( C ) STRANDEDNESS: unknown
( D ) TOPOLOGY: unknown ( i i ) MOLECULE TYPE: DNA ( x i ) SEQUENCE DESCRIPTION: SEQ ID NO:2:

TTGNNNGCTT    CCAANNNNNT    GGT                                                           23

( 2 ) INFORMATION FOR SEQ ID NO:3:

( i ) SEQUENCE CHARACTERISTICS:
( A ) LENGTH: 22 base pairs
( B ) TYPE: nucleic acid
( C ) STRANDEDNESS: unknown (D) TOPOLOGY: unknown (ii) MOLECULE TYPE: DNA (xi) SEQUENCE DESCRIPTION: SEQ ID NO:3:

GTTCCTCAA GGCAAGAACT CC    22

(2) INFORMATION FOR SEQ ID NO:4:

(i) SEQUENCE CHARACTERISTICS:
(A) LENGTH: 24 base pairs
(B) TYPE: nucleic acid
(C) STRANDEDNESS: unknown
(D) TOPOLOGY: unknown (ii) MOLECULE TYPE: DNA (xi) SEQUENCE DESCRIPTION: SEQ ID NO:4:

TCGACCCAGG TTTCATGAAC GATG    24

(2) INFORMATION FOR SEQ ID NO:5:

(i) SEQUENCE CHARACTERISTICS:
(A) LENGTH: 31 base pairs
(B) TYPE: nucleic acid
(C) STRANDEDNESS: unknown
(D) TOPOLOGY: unknown (ii) MOLECULE TYPE: DNA (xi) SEQUENCE DESCRIPTION: SEQ ID NO:5:

TCCTGCAGCA ACCAATGAGG AGAATGACAA C    31

(2) INFORMATION FOR SEQ ID NO:6:

(i) SEQUENCE CHARACTERISTICS:
(A) LENGTH: 23 base pairs
(B) TYPE: nucleic acid
(C) STRANDEDNESS: unknown
(D) TOPOLOGY: unknown (ii) MOLECULE TYPE: DNA (xi) SEQUENCE DESCRIPTION: SEQ ID NO:6:

TTGNNNNNTT CCAANNNNNT GGT    23

(2) INFORMATION FOR SEQ ID NO:7:

(i) SEQUENCE CHARACTERISTICS:
(A) LENGTH: 25 base pairs
(B) TYPE: nucleic acid
(C) STRANDEDNESS: unknown
(D) TOPOLOGY: unknown (ii) MOLECULE TYPE: DNA (xi) SEQUENCE DESCRIPTION: SEQ ID NO:7:

AATTNNNNNT GGTTCCANNN NNNNA    25

(2) INFORMATION FOR SEQ ID NO:8:

(i) SEQUENCE CHARACTERISTICS:
(A) LENGTH: 30 base pairs
(B) TYPE: nucleic acid
(C) STRANDEDNESS: unknown
(D) TOPOLOGY: unknown (ii) MOLECULE TYPE: DNA (xi) SEQUENCE DESCRIPTION: SEQ ID NO:8:

GATGGATTCA GGAGAAATTG TTCTGCCATC    30

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:9:

GATTCCTCAA GGTATGCCTC TCC    23

(2) INFORMATION FOR SEQ ID NO:10:

(i) SEQUENCE CHARACTERISTICS:
        (A) LENGTH: 15 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:10:

TTCCAATTGG TTGGT    15

(2) INFORMATION FOR SEQ ID NO:11:

(i) SEQUENCE CHARACTERISTICS:
        (A) LENGTH: 45 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:11:

CACCACCTAG AACTAGGATA TCAAACTCTT CGGGGATAGC CATCG    45

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:12:

CGATGGCTAT CCCCGAAG    18

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:13:

TTGCACTCTG TTGGCTCATG ACGAT    25

(2) INFORMATION FOR SEQ ID NO:14:

( i ) SEQUENCE CHARACTERISTICS:
  ( A ) LENGTH: 26 base pairs
  ( B ) TYPE: nucleic acid
  ( C ) STRANDEDNESS: unknown
  ( D ) TOPOLOGY: unknown ( i i ) MOLECULE TYPE: DNA ( x i ) SEQUENCE DESCRIPTION: SEQ ID NO:14:

CAAGCTTGCA CAAACGAACG TCTCAC                    26

( 2 ) INFORMATION FOR SEQ ID NO:15:

( i ) SEQUENCE CHARACTERISTICS:
  ( A ) LENGTH: 90 base pairs
  ( B ) TYPE: nucleic acid
  ( C ) STRANDEDNESS: unknown
  ( D ) TOPOLOGY: unknown ( i i ) MOLECULE TYPE: DNA ( x i ) SEQUENCE DESCRIPTION: SEQ ID NO:15:

CATCATTATC AGCTTACTTT CATAATTGTG ACTGGTTCCA ACCGACAAGC TTGCATGCAG   60

GTGCTGAACA CCATGGTGAA CAAACACTTC                 90

( 2 ) INFORMATION FOR SEQ ID NO:16:

( i ) SEQUENCE CHARACTERISTICS:
  ( A ) LENGTH: 16 base pairs
  ( B ) TYPE: nucleic acid
  ( C ) STRANDEDNESS: unknown
  ( D ) TOPOLOGY: unknown ( i i ) MOLECULE TYPE: DNA ( x i ) SEQUENCE DESCRIPTION: SEQ ID NO:16:

CGATGTATCC CCGAAG                        16

( 2 ) INFORMATION FOR SEQ ID NO:17:

( i ) SEQUENCE CHARACTERISTICS:
  ( A ) LENGTH: 15 amino acids
  ( B ) TYPE: amino acid
  ( C ) STRANDEDNESS: unknown
  ( D ) TOPOLOGY: unknown ( i i ) MOLECULE TYPE: protein ( x i ) SEQUENCE DESCRIPTION: SEQ ID NO:17:

Ala Ile Pro Glu Glu Phe Asp Ile Ile Val Cys Gly Gly Gly Ser
  1       5          10         15

( 2 ) INFORMATION FOR SEQ ID NO:18:

( i ) SEQUENCE CHARACTERISTICS:
  ( A ) LENGTH: 30 base pairs
  ( B ) TYPE: nucleic acid
  ( C ) STRANDEDNESS: unknown
  ( D ) TOPOLOGY: unknown ( i i ) MOLECULE TYPE: DNA ( x i ) SEQUENCE DESCRIPTION: SEQ ID NO:18:

CTGGTCTAGA CATTGTATGC TTCCAAGTTT                 30

( 2 ) INFORMATION FOR SEQ ID NO:19:

( i ) SEQUENCE CHARACTERISTICS:

( A ) LENGTH: 30 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:19:

TTGGAAGCAT ACAATGTCTA GACCAGAAAC 30

( 2 ) INFORMATION FOR SEQ ID NO:20:

( i ) SEQUENCE CHARACTERISTICS:
        ( A ) LENGTH: 39 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:20:

ATGCATTGTT CTCCACATTG TATGCTTCCA AGTTTCTGG 39

( 2 ) INFORMATION FOR SEQ ID NO:21:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:21:

CTGGTCTAGA CATTGTATGC TTCCAAGTTT 30

( 2 ) INFORMATION FOR SEQ ID NO:22:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:22:

TTGGAAGCAT ACAATGTCTA GACCAGAAAC 30

( 2 ) INFORMATION FOR SEQ ID NO:23:

( i ) SEQUENCE CHARACTERISTICS:
        ( A ) LENGTH: 69 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:23:

ATGCATTGTT CTCCACATTG TATGCTTCCA AGTTTCTGGT CTAGACATTG TATGCTTCCA 60

AGTTTCTGG 69

( 2 ) INFORMATION FOR SEQ ID NO:24:

( i ) SEQUENCE CHARACTERISTICS:
        ( A ) LENGTH: 23 base pairs
        ( B ) TYPE: nucleic acid
        ( C ) STRANDEDNESS: unknown (D) TOPOLOGY: unknown (ii) MOLECULE TYPE: DNA (xi) SEQUENCE DESCRIPTION: SEQ ID NO:24:

```
TTGTATGCTT CCAAGTTTCT GGT                                              23
```

(2) INFORMATION FOR SEQ ID NO:25:

(i) SEQUENCE CHARACTERISTICS:
        (A) LENGTH: 15 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:25:

```
ACACCCGCTT TTTGG                                                       15
```

(2) INFORMATION FOR SEQ ID NO:26:

(i) SEQUENCE CHARACTERISTICS:
        (A) LENGTH: 162 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:26:

```
TTCTCCTGGC ACTATTTGC TTCTTATCAG TCTATCTTTG AGTTGGTGAA TATCTTGAGA       60
CATGGGCTTG GGGAAATCAT TTGATTTCGA AGTTTGCTT GGTAGTTGAC ATTCTTCTTC      120
GGAGTATAAA AGATTAGTG AGACGTTCGT TTGTGCAAGC TT                         162
```

(2) INFORMATION FOR SEQ ID NO:27:

(i) SEQUENCE CHARACTERISTICS:
        (A) LENGTH: 162 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:27:

```
TTTCTTCTCG TACGAGCTTG CCCTGATCAG CCTATCTCGC AGCTGATGAA TATCTTGTGG      60
TAGGGGTTTG GGAAAATCAT TCGAGTTTGA TGTTTTCTT GGTATTTCCC ACTCCTCTTC      120
AGAGTACAGA AGATTAAGTG AGACGTTCGT TTGTGCAAGC TT                        162
```

(2) INFORMATION FOR SEQ ID NO:28:

(i) SEQUENCE CHARACTERISTICS:
        (A) LENGTH: 137 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:28:

```
TTTCATTTCT TTTTATACGT ACGTATATGT ACTAGATGAA GAATGCGACA AGGCCGACCA      60
ACAGCAATGG TGCTTGGTAC CAAAGTTTGG AAGGTGCTAC CGAATTGGCC GATGATATTG     120
AGTGGAGTTG TCATTCT                                                    137
```

( 2 ) INFORMATION FOR SEQ ID NO:29:

( i ) SEQUENCE CHARACTERISTICS:
    ( A ) LENGTH: 974 base pairs
    ( B ) TYPE: nucleic acid
    ( C ) STRANDEDNESS: unknown
    ( D ) TOPOLOGY: unknown ( i i ) MOLECULE TYPE: DNA ( x i ) SEQUENCE DESCRIPTION: SEQ ID NO:29:

| | | | | | | |
|---|---|---|---|---|---|---|
| GTAAGTGAGA | TCCAACACCC | AGGAACGAGA | TGGATTCAGG | AGAAATTGTT | CTGCCATCCG | 60 |
| ACATCGACAA | GTTAGACACA | ATAGTGCCAA | ATGCAGAGGG | GACGTTTCCT | CAAGGCAAGA | 120 |
| ACTCCACTTT | ATTCCTCCTC | AAACACCCGC | CTTCGCCGTT | AAAACCAGC | CCAGTTACTA | 180 |
| AACATGGTTT | GGACTCTCTC | TAATCCACTT | TGTTAGGCTA | CTAGTAGCAT | TATTTCTTA | 240 |
| GCCTGTCTAT | ATGGTTCCTT | GCGAGTTTTT | AATTTATTT | CTATTTCCGA | ATGTAACTTA | 300 |
| CTCCGCATTC | CATCCCAACA | CCAGAAAGTT | GAGGGTTTTT | GTGAGTGTGG | GGTCGGTAAC | 360 |
| AGTTTCATGT | TCCCCCAATG | GCCTAAAATT | GACACTTTAG | ACGCCCTGTT | CAAACTCAAA | 420 |
| TTGACAAAAG | CGTGATCTCA | TCAGAGATGA | ACTAGGTTTG | GTTCGATCAA | AAGCTAACGG | 480 |
| CCAGTTGGTC | AAAAGAAAC | TTCCAATGTC | GGCATACCGT | TTGTTTCGTT | TGACCCGACA | 540 |
| ATTGATGTTG | AAGAATTCCC | TCTTACACTT | AGCGCAGCCT | TTATTTGCT | TGGGGTCTCG | 600 |
| CTGCGCTTGG | GTCTCGGTGT | GCTTGTGACC | GGAAACGCAA | ATGGGGAAAC | ACCCGCTTTT | 660 |
| TGGATGATTA | TGCATTGTTC | TCCACATTGT | ATGCTTCCAA | GTTCTGGTG | GAATACTGA | 720 |
| TAGCCTAACG | TTCATGATCA | AAACTAATGT | CTTCCCTACT | TGAACAGCAA | TATATAAACA | 780 |
| GAAGAAGATT | TCCTTTCTAA | GGTCTTTTTT | TTTATCATCA | TTATCAGCTT | ACTTTCATAA | 840 |
| TTGTGACTGG | TTCCAATTGA | CAAGCTTTTG | ATTCTAACGA | CTTTAACGAC | AACCTAAAGA | 900 |
| ACAAAAACAA | CTAATTATTC | GAAACAATGG | CTATTCCCGA | AGAATTGAT | ATTATCGTCT | 960 |
| GTGGTGGTGG | ATCC | | | | | 974 |

( 2 ) INFORMATION FOR SEQ ID NO:30:

( i ) SEQUENCE CHARACTERISTICS:
    ( A ) LENGTH: 971 base pairs
    ( B ) TYPE: nucleic acid
    ( C ) STRANDEDNESS: unknown
    ( D ) TOPOLOGY: unknown ( i i ) MOLECULE TYPE: DNA ( x i ) SEQUENCE DESCRIPTION: SEQ ID NO:30:

| | | | | | | |
|---|---|---|---|---|---|---|
| TCTAACATCC | AAAGACGAAA | GGTTGAATGA | AACCTTTTG | CCATCCGACA | TCCACAGGTC | 60 |
| CATTCTCACA | CATAAGTGCC | AAACGCAACA | GGAGGGGATA | CACTAGCAGC | AGACGTTGCA | 120 |
| AACGCAGGAC | TCATCCTCTT | CTCTAACACC | ATTTTGCATG | AAAACAGCCA | GTTATGGGCT | 180 |
| TGATGGAGCT | CGCTCATTCC | AATTCCTTCT | ATTAGGCTAC | TAACACCATG | ACTTTATTAG | 240 |
| CCTGTCTATC | CTGGCCCCCC | TGGCGAGGTC | ATGTTTGTTT | ATTTCCGAAT | GCAACAAGCT | 300 |
| CCGCATTACA | CCCGAACATC | ACTCCAGATG | AGGGCTTTCT | GAGTGTGGGG | TCAAATAGTT | 360 |
| TCATGTTCCC | AAATGGCCCA | AAACTGACAG | TTTAAACGCT | GTCTTGGAAC | CTAATATGAC | 420 |
| AAAAGCGTGA | TCTCATCCAA | GATGAACTAA | GTTGGTTCG | TTGAAATCCT | AACGGCAGT | 480 |
| TGGTCAAAAA | GAAACTTCCA | AAAGTCGCCA | TACCGTTTGT | CTTGTTTGGT | ATTGATTGAC | 540 |
| GAATGCTCAA | AATAATCTC | ATTAATGCTT | AGCGCAGTCT | CTCTATCGCT | TCTGAACCCG | 600 |

| GTGGCACCTG | TGCCGAAACG | CAAATGGGGA | AACAACCCGC | TTTTTGGATG | ATTATGCATT | 660 |
| GTCTCCACAT | TGTATGCTTC | CAAGATTCTG | GTGGGAATAC | TGCTGATAGC | CTAACGTTCA | 720 |
| TGATCAAAAT | TTAACTGTTC | TAACCCCTAC | TTGGACAGGC | AATATATAAA | CAGAAGGAAG | 780 |
| CTGCCCTGTC | TTAAACCTTT | TTTTTATCA | TCATTATTAG | CTTACTTTCA | TAATTGCGAC | 840 |
| TGGTTCCAAT | TGACAAGCTT | TTGATTTTAC | GACTTTTAAC | GACAACTTGA | GAAGATCAAA | 900 |
| AAACAACTAA | TTATTCGAAA | CGATGGCTAT | CCCCGAAGAG | TTTGATTATC | CTAGTTCTAG | 960 |
| GTGGTGGATC | C | | | | | 971 |

(2) INFORMATION FOR SEQ ID NO:31:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:31:

TCAAAAAGAA ACTTCCAATG TCGGCATA        28

(2) INFORMATION FOR SEQ ID NO:32:

(i) SEQUENCE CHARACTERISTICS:
        (A) LENGTH: 29 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:32:

TCAAAAAGAA ACTTCCAAAA GTCGCCATA        29

(2) INFORMATION FOR SEQ ID NO:33:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:33:

ACATTGTATG CTTCCAAGTT TCTGGTGG        28

(2) INFORMATION FOR SEQ ID NO:34:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:34:

ACATTGTATG CTTCCAAGAT TCTGGTGG        28

(2) INFORMATION FOR SEQ ID NO:35:

(i) SEQUENCE CHARACTERISTICS:
        (A) LENGTH: 30 base pairs
        (B) TYPE: nucleic acid ( C ) STRANDEDNESS: unknown
( D ) TOPOLOGY: unknown ( i i ) MOLECULE TYPE: DNA ( x i ) SEQUENCE DESCRIPTION: SEQ ID NO:35:

ACAGTTGGGA GTTTCCAATT GGTTGGTTTT    30

( 2 ) INFORMATION FOR SEQ ID NO:36:

( i ) SEQUENCE CHARACTERISTICS:
       ( A ) LENGTH: 29 base pairs
       ( B ) TYPE: nucleic acid
       ( C ) STRANDEDNESS: unknown
       ( D ) TOPOLOGY: unknown ( i i ) MOLECULE TYPE: DNA ( x i ) SEQUENCE DESCRIPTION: SEQ ID NO:36:

TGTGCTGGAT GCNACCAATT AATTGTTGC    29

( 2 ) INFORMATION FOR SEQ ID NO:37:

( i ) SEQUENCE CHARACTERISTICS:
       ( A ) LENGTH: 28 base pairs
       ( B ) TYPE: nucleic acid
       ( C ) STRANDEDNESS: unknown
       ( D ) TOPOLOGY: unknown ( i i ) MOLECULE TYPE: DNA ( x i ) SEQUENCE DESCRIPTION: SEQ ID NO:37:

GGCTTTGGTC ATTTNCAATG TTGTCGTC    28

( 2 ) INFORMATION FOR SEQ ID NO:38:

( i ) SEQUENCE CHARACTERISTICS:
       ( A ) LENGTH: 27 base pairs
       ( B ) TYPE: nucleic acid
       ( C ) STRANDEDNESS: unknown
       ( D ) TOPOLOGY: unknown ( i i ) MOLECULE TYPE: DNA ( x i ) SEQUENCE DESCRIPTION: SEQ ID NO:38:

AAAATGCTCT TTTCCATCAT CATCATC    27

( 2 ) INFORMATION FOR SEQ ID NO:39:

( i ) SEQUENCE CHARACTERISTICS:
       ( A ) LENGTH: 30 base pairs
       ( B ) TYPE: nucleic acid
       ( C ) STRANDEDNESS: unknown
       ( D ) TOPOLOGY: unknown ( i i ) MOLECULE TYPE: DNA ( x i ) SEQUENCE DESCRIPTION: SEQ ID NO:39:

GTCTTTGATG TCTTCCANCC ATCTGCAGAT    30

( 2 ) INFORMATION FOR SEQ ID NO:40:

( i ) SEQUENCE CHARACTERISTICS:
       ( A ) LENGTH: 23 base pairs
       ( B ) TYPE: nucleic acid
       ( C ) STRANDEDNESS: unknown
       ( D ) TOPOLOGY: unknown ( i i ) MOLECULE TYPE: DNA ( x i ) SEQUENCE DESCRIPTION: SEQ ID NO:40:

TTGNNNNNTT CCAANNNNNT GGT                                     23

( 2 ) INFORMATION FOR SEQ ID NO:41:

( i ) SEQUENCE CHARACTERISTICS:
       ( A ) LENGTH: 29 base pairs
       ( B ) TYPE: nucleic acid
       ( C ) STRANDEDNESS: unknown
       ( D ) TOPOLOGY: unknown ( i i ) MOLECULE TYPE: DNA ( x i ) SEQUENCE DESCRIPTION: SEQ ID NO:41:

AATTGTGACT GGTTCCAATT GACAAGCTT                               29

( 2 ) INFORMATION FOR SEQ ID NO:42:

( i ) SEQUENCE CHARACTERISTICS:
       ( A ) LENGTH: 29 base pairs
       ( B ) TYPE: nucleic acid
       ( C ) STRANDEDNESS: unknown
       ( D ) TOPOLOGY: unknown ( i i ) MOLECULE TYPE: DNA ( x i ) SEQUENCE DESCRIPTION: SEQ ID NO:42:

AATTGCGACT GGTTCCAATT GACAAGCTT                               29

( 2 ) INFORMATION FOR SEQ ID NO:43:

( i ) SEQUENCE CHARACTERISTICS:
       ( A ) LENGTH: 28 base pairs
       ( B ) TYPE: nucleic acid
       ( C ) STRANDEDNESS: unknown
       ( D ) TOPOLOGY: unknown ( i i ) MOLECULE TYPE: DNA ( x i ) SEQUENCE DESCRIPTION: SEQ ID NO:43:

AATTCTNTAT GCTACCGTGC AGCGACTC                                28

( 2 ) INFORMATION FOR SEQ ID NO:44:

( i ) SEQUENCE CHARACTERISTICS:
       ( A ) LENGTH: 28 base pairs
       ( B ) TYPE: nucleic acid
       ( C ) STRANDEDNESS: unknown
       ( D ) TOPOLOGY: unknown ( i i ) MOLECULE TYPE: DNA ( x i ) SEQUENCE DESCRIPTION: SEQ ID NO:44:

AATTTAGCCT CGTTCCAGCC ATTCACGG                                28

( 2 ) INFORMATION FOR SEQ ID NO:45:

( i ) SEQUENCE CHARACTERISTICS:
       ( A ) LENGTH: 26 base pairs
       ( B ) TYPE: nucleic acid
       ( C ) STRANDEDNESS: unknown
       ( D ) TOPOLOGY: unknown ( i i ) MOLECULE TYPE: DNA ( x i ) SEQUENCE DESCRIPTION: SEQ ID NO:45:

AATTNNGNCT GGTTCCANNN NNNNAN                                  26

( 2 ) INFORMATION FOR SEQ ID NO:46:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:46:

ACACCCGCTT TTTGG     15

( 2 ) INFORMATION FOR SEQ ID NO:47:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:47:

CAACCCGCTT TTTGG     15

( 2 ) INFORMATION FOR SEQ ID NO:48:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:48:

AAAACCCCTT TTATG     15

( 2 ) INFORMATION FOR SEQ ID NO:49:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:49:

ATCCCCAGTT TTTGC     15

( 2 ) INFORMATION FOR SEQ ID NO:50:

( i ) SEQUENCE CHARACTERISTICS:
        ( A ) LENGTH: 14 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:50:

AATTACTCTT TTGG     14

( 2 ) INFORMATION FOR SEQ ID NO:51:

( i ) SEQUENCE CHARACTERISTICS:
        ( A ) LENGTH: 15 base pairs
        ( B ) TYPE: nucleic acid ( C ) STRANDEDNESS: unknown
( D ) TOPOLOGY: unknown ( i i ) MOLECULE TYPE: DNA ( x i ) SEQUENCE DESCRIPTION: SEQ ID NO:51:

| CGCAAGCCTT TTTGC | 15 |
|---|---|

( 2 ) INFORMATION FOR SEQ ID NO:52:

( i ) SEQUENCE CHARACTERISTICS:
        ( A ) LENGTH: 10 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:52:

| CCNCTTTTTG | 10 |
|---|---|

( 2 ) INFORMATION FOR SEQ ID NO:53:

( i ) SEQUENCE CHARACTERISTICS:
        ( A ) LENGTH: 345 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:53:

| CAAAACGCTC | CCACTCTGGG | TGGTGAAGAC | TTAGGATACT | CTGGGTCATG | CCCTGGACAT | 60 |
|---|---|---|---|---|---|---|
| GACTGTTCCT | CAGTTCAAGT | TGGGAACTTA | CGAGAAGACT | GGTCTTGCTA | GATTCTAGTT | 120 |
| TGTTCTGTCN | NCGAATATTT | TTTTAAATGA | TTGATTTTTC | CTGTCAACAT | TGTTTAGTTA | 180 |
| TTTATGTCGT | TATAGTCACT | AANACAGTTT | AGCTTCTTNG | GAATTTTTC | TCTCGTACCA | 240 |
| CACAGATACT | AGANNTAGAA | TGCACCCACA | GCGACTAATA | NCAACGGAGC | TTGATACCNC | 300 |
| AGGTTAGGAG | GTGCTACGGA | ATTGNCCCAT | GATATCTCCG | TAGAG | | 345 |

( 2 ) INFORMATION FOR SEQ ID NO:54:

( i ) SEQUENCE CHARACTERISTICS:
        ( A ) LENGTH: 348 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:54:

| GAAAAGACTG | CCACCTTGGT | TGGTGAAGAC | TTAGGATACA | CAGGTGANGC | CTTAGACATG | 60 |
|---|---|---|---|---|---|---|
| ACTGTACCTC | AGTTCAAGTT | GGGCACTTAC | GAGAAGACTG | GTCTTGCTAG | ATTCTAGTTT | 120 |
| ATGTTGTATC | TATGAATATT | TTTTACATG | GTGGATTTGT | TCCAATCTAG | TTGTTAGTTA | 180 |
| TTTGTCGTTA | TAGTCACTAA | TACAGTTACC | ATCGGAATCT | TTCATTTCT | TTTTATACGT | 240 |
| ACGTATATGT | ACTAGATGAA | GAATGCGACA | AGGCCGACCA | ACAGCAATGG | TGCTTGGTAC | 300 |
| CAAAGTTTGG | AAGGTGCTAC | CGAATTGGCC | GATGATATTG | AAGTGGAG | | 348 |

( 2 ) INFORMATION FOR SEQ ID NO:55:

( i ) SEQUENCE CHARACTERISTICS:
        ( A ) LENGTH: 349 base pairs
        ( B ) TYPE: nucleic acid ( C ) STRANDEDNESS: unknown
( D ) TOPOLOGY: unknown ( i i ) MOLECULE TYPE: DNA ( x i ) SEQUENCE DESCRIPTION: SEQ ID NO:55:

| | | | | | | |
|---|---|---|---|---|---|---|
| GAAAAGACTG | CCACTTTGCT | TGGAGAAGAT | TTAGGATACT | CTGGTGANGC | CTTAGACATG | 60 |
| ACTGTTCCTC | ACTTCAAGTT | GGGCACTTAC | GAGAAGACCG | GTCTTGCTAG | ATTCTAATCA | 120 |
| AGAGGATGTC | AGAATGCCAT | TTGCCTGAGA | GATGCAGGCT | TCATTTTGA | TACTTTTTA | 180 |
| TTTGTAACCT | ATATAGTATA | GGATTTTTTT | TGTCATTTTG | TTTCTTCTCG | TACGAGCTTG | 240 |
| CTCCTGATCA | GCCTATCTCG | CAGCTGATGA | ATATCTTGTG | GTAGGGGTTT | GGGAAAATCA | 300 |
| TTCGAGTTTG | ATGTTTTCT | TGGTATTTCC | CACTCCTCTT | CAGAGTACA | | 349 |

( 2 ) INFORMATION FOR SEQ ID NO:56:

( i ) SEQUENCE CHARACTERISTICS:
( A ) LENGTH: 38 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:56:

Glu Lys Thr Ala Thr Leu Val Gly Glu Asp Leu Gly Tyr Ser Gly Glu
1               5                   10                  15

Ala Leu Asp Met Thr Val Pro Gln Phe Lys Leu Gly Thr Tyr Glu Lys
            20                  25                  30

Thr Gly Leu Ala Arg Phe
            35

( 2 ) INFORMATION FOR SEQ ID NO:57:

( i ) SEQUENCE CHARACTERISTICS:
( A ) LENGTH: 128 base pairs
( B ) TYPE: nucleic acid
( C ) STRANDEDNESS: unknown
( D ) TOPOLOGY: unknown ( i i ) MOLECULE TYPE: DNA ( x i ) SEQUENCE DESCRIPTION: SEQ ID NO:57:

| | | | | | | |
|---|---|---|---|---|---|---|
| TTCTCCTGGC | ACTATTTGC | TTCTTATCAG | TCTATCTTTG | AGTTGGTGAA | TATCTTGAGA | 60 |
| CATGGGCTTG | GGGAAATCAT | TTGATTTCGA | AGTTTGCTT | GGTAGTTGAC | ATTCTTCTTC | 120 |
| GGACTATA | | | | | | 128 |

What is claimed is:

1. A method of converting starch into ethanol comprising the step, growing yeast cells in a culture medium, wherein said yeast cells comprise a genetic construction, said genetic construction comprising a starch degrading enzyme encoding nucleotide sequence operatively linked with the regulatory region of ZZA1, wherein the regulatory region is located 5' to the starch degrading enzyme encoding polynucleotide sequence.

2. A method according to claim 1, wherein said starch degrading enzyme is α-amylase.

3. A method according to claim 1, wherein said regulatory region has been modified to delete the sequence GTTTCCTCAAGGCAAGAACTCC (SEQ ID No:3).

4. A method according to claim 1, wherein said regulatory region is derived from gene ZZA1.

5. A method according to claim 1, wherein said regulatory region comprises the regulatory region of alcohol oxidase gene ZZA1, wherein said genetic construction comprises the non-coding region of the nucleotide sequence of FIG. 9 (SEQ ID. NO.: 1).

* * * * *